US008178297B2

(12) United States Patent
Mickelson et al.

(10) Patent No.: US 8,178,297 B2
(45) Date of Patent: May 15, 2012

(54) METHOD OF DETECTING CANINE EXERCISE-INDUCED COLLAPSE

(76) Inventors: James R. Mickelson, Roseville, MN (US); Katie Minor, Saint Paul, MN (US); Susan M. Taylor, Saskatoon (CA); Edward Earl Patterson, Saint Paul, MN (US)

(*) Notice: Subject to any disclaimer, the term of this patent is extended or adjusted under 35 U.S.C. 154(b) by 197 days.

(21) Appl. No.: 12/668,634

(22) PCT Filed: Apr. 8, 2009

(86) PCT No.: PCT/US2009/039944
§ 371 (c)(1),
(2), (4) Date: Jan. 11, 2010

(87) PCT Pub. No.: WO2009/126733
PCT Pub. Date: Oct. 15, 2009

(65) Prior Publication Data
US 2010/0196900 A1    Aug. 5, 2010

Related U.S. Application Data

(60) Provisional application No. 61/123,753, filed on Apr. 9, 2008.

(51) Int. Cl.
*C07H 21/04* (2006.01)
*C12Q 1/68* (2006.01)

(52) U.S. Cl. ...... 435/6.1; 435/6.11; 435/6.12; 435/91.1; 435/91.2; 536/23.1; 536/24.3

(58) Field of Classification Search .................. None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 2006/0147962 A1 | 7/2006 | Jones et al. |

FOREIGN PATENT DOCUMENTS
WO    WO 2005/116265    12/2005

OTHER PUBLICATIONS

Axlund, T.W., "Exercise induced collapse in dogs", *In: Proceedings of the Western Veterinary Conference*, VET-244, 2 pages, (2004).
Breen, M., et al., "An integrated 4249 marker FISH/RH map of the canine genome", *BMC Genomics* 5(1), 62 (11pages), (2004).
Clark, S.G., et al., "A dynamin GTPpase mutation causes a rapid and reversible temperature-inducible locomotion defect in *C. elegan*", *Proc. Natl. Acad. Sci. USA.*, 94, 10438-10443, (1997).
Database EMBL [Online], "Sequence 90290 from Patent WO2005116265", EBI Accession No. EMBL: HA869105, 1 page, (Jun. 5, 2009).

Database NCBI REF SEQ[Online], "Predicted: *Canis familiaris* similar to Dynamin-1, transcript variant 1", retrieved from *NCBI Database Accession No. XM_845686*, 2 pages, (Aug. 30, 2005).
Database NCBI REF SEQ[Online], "Predicted: *Canis familiaris* similar to Dynamin-1, transcript variant 2", retrieved from *NCBI Database Accession No. XM_857171*, 2 pages, (Aug. 30, 2005).
Grigliatti, T.A., et al., "Temperature-sensitive mutation in *Drosophila melanogaster*. XIV. A selection on immobile adults,", *Mol. Gen. Genet.*, 120, 107-114, (1973).
Guyon, R., et al., "A 1-Mb Resolution Radiation Hybrid Map of the Canine Genome" *Proc. Natl. Acad. Sci. U.S.A.*, 100(9), 5296-5301, (2003).
Lander, E. and L. Kruglyak, "Genetic dissection of complex traits: guidelines for interpreting and reporting linkage results", *Nature Genet.*, 11(3), 241-247, (1995).
Nielsen, P.E., et al., "Sequence-selective recognition of DNA by strand displacement with a thymine-substituted polyamide", *Science*, 254(5037), 1497-1500, (1991).
Patterson, E.E., et al., "A canine dynamin 1 (*DNM1*) mutation is highly associated with the syndrome of exercise-induced collapse", *Nature Genetics*, 40, 1235-1239 and 15 pages of online supporting materials, (2008).
Patterson, E.E., et al., "A dynamin 1 (*DNM1*) mutation is highly associated with the syndrome of exercise-induced collapse in Labrador retrievers" *4th International Meeting on Canine and Feline Genomics and Inherited Diseases*, St. Malo France, 22 pages, (May 2008).
Pelé, M., et al., "SINE exonic insertion in the PTPLA gene leads to multiple splicing defects and segregates with the autosomal recessive centronuclear myopathy in dog", *Human Mol. Gen.*, 14(11), 1417-1427, (2005), and "Erratum: SINE exonic insertion in the PTPLA gene leads to multiple splicing defects and segregates with the autosomal recessive centronuclear myopathy in dog", *Human Mol. Gen.*, 14(13), 1905-6, (2005).
Shelton, G.D., "Exercise intolerance in dogs", American College of Veterinary Internal Medicine Scientific Forum, May, Washington, D.C., *In: Proceedings of the 11th ACVIM Forum*, 888-891, (1993).
Shelton, G.D. and E. Engvall, "Muscular dystrophies and other inherited myopathies", *Vet. Clin. North Am. Small Anim. Pract.*, 32, 103-124, (2002).
Shelton, G.D., et al., "The syndrome of exercise induced collapse in Labrador Retrievers", American College of Veterinary Internal Medicine Scientific Forum, June, Dallas, TX, *In: Proceedings of the 20th ACVIM Forum*, 317-318, (2002).
Stephens, M. et al., "A new statistical method for haplotype reconstruction from population data", *Am. J. Hum. Genet.*, 68(4), 978-989, (2001). Taylor, S.M., et al., "Exercise Induced Collapse in Labrador Retrievers", 8 pages, (Jan. 3, 2008), http://www.thelabradorclub.com/uploads/file/Exercise%20Induce%20Collapse.pdf.
Taylor, S.M., "Exercise induced weakness/collapse in Labrador Retrievers", *In: Tilley LP, Smith FW, eds. Blackwell's Five Minute Veterinary Consult: Canine and Feline. 4th ed.*, Blackwell Publishing, Williston, Vermont, 458-459, (2007).
Taylor, S.M. and G.D. Shelton, "The syndrome of exercise induced collapse in Labrador Retrievers", American College of Veterinary Internal Medicine Scientific Forum, June, Dallas, TX, *In: Proceedings of the 20th ACVIM Forum*, 315-316, (2002).
Taylor, S.M., et al., "Evaluations of Labrador retrievers with Exercise-induced collapse, including response to a standardized strenuous exercise protocol", *J. American Animal Hospital Association*, 45, 3-13, (2009).
Taylor, S.M., et al., "Exercise-Induced Collapse of Labrador retrievers: Survey results and preliminary investigation of heritability", *J. American Animal Hospital Association*, 44, 295-301, (2008).
Patent Cooperation Treaty, International Search Report & Written Opinion of the International Search Authority, PCT/US2009/039944, Sep. 22, 2009, 20 pages.

*Primary Examiner* — Jeanine A Goldberg
(74) *Attorney, Agent, or Firm* — Viksnins Harris & Padys PLLP

(57) ABSTRACT

The present invention relates to diagnosing Canine Exercise-Induced Collapse (EIC).

8 Claims, 18 Drawing Sheets

Figure 1.

```
   1 ATGGGCAACC GCGGCATGGA GGATCTCATC CCGCTAGTCA ACCGGCTGCA GGACGCCTTC
  61 TCCGCTATCG GCCAGAACGC GGACCTCGAC CTACCGCAGA TCGCGGTGGT GGGCGGCCAG
 121 AGCGCCGGCA AGAGCTCGGT GCTCGAGAAT TTCGTAGGCA GGGACTTCCT GCCCCGAGGG
 181 TCAGGCATTG TCACCCGACG GCCCCTGGTC CTGCAGCTGG TCAATGCCAC CACAGAATAT
 241 GCCGAATTCC TGCACTGCAA GGGGAAGAAA TTCACTGACT TCGAGGAGGT ACGCCTGGAG
 301 ATCGAGGCTG AGACCGACCG GGTCACTGGC ACCAACAAGG GCATCTCGCC GGTGCCCATC
 361 AACCTCCGCG TCTACTCGCC TCAGGTCCTG AATCTGACAC TGGTGGACCT ACCCGGAATG
 421 ACCAAGGTCC CAGTGGGGGA CCAACCTCCT GACATCGAGT TCCAGATCCG GGACATGCTT
 481 ATGCAGTTCG TCACCAAAGA GAACTGCCTC ATCCTGGCTG TGTCCCCCGC CAACTCCGAC
 541 CTGGCCAACT CTGATGCTCT CAAGGTTGCC AAGGAGGTGG ACCCCAGGG TCAGCGCACC
 601 ATYGGGGTCA TCACCAAGCT AGATCTGATG GAYGAGGGCA CAGATGCCCG AGATGTGCTA
 661 GAGAATAAGC TCCTTCCCCT GCGCAGAGGC TACATAGGGG TGGTAAACCG AAGCCAGAAG
 721 GACATTGATG GCAAGAAGGA CATCTCAGCT GCCTTGGCYG CTGAACGCAA GTTCTTTCTC
 781 TCCCACCCAT CCTACCGCCA CTTGGCGGAC CGCATGGGCA CACCCTACCT ACAGAAGGTC
 841 CTCAACCAGC AACTGACCAA CCACATCCGG GACACACTGC CGGGGCTCCG GAACAGGCTG
 901 CAGAGCCAGC TACTGTCCAT TGAGAAGGAG GTGGAGGAGT ACAAGAACTT CCGACCTGAT
 961 GACCCAGCAC GCAAGACCAA GGCCCTGCTG CAGATGGTCC AGCAGTTTGC TGTGGACTTT
1021 GAGAAGCGCA TTGAGGGCTC CGGGGACCAG ATTGACACCT ATGAACTGTC AGGGGGAGCC
1081 CGCATCAACC GGATCTTCCA TGAGCGCTTC CCCTTTGAGC TAGTCAAGAT GGAGTTTGAT
1141 GAGAAGGAGC TCCGAGAGA GATCAGCTAC GCCATCAAGA ACATCCATGG CATTAGAACG
1201 GGGCTCTTTA CCCCAGACAT GGCTTTTGAG ACCATTGTGA AAAAGCAGGT GAAGAAGATC
1261 CGAGAACCGT GTCTCAAGTG TGTGGACATG GTTATCTCGG AACTAATCAG CACGGTTAGA
1321 CAGTGCACCA AGAAGCTGCA GCAGTACCCC CGGCTGCGGG AGGAGATGGA GCGCATCGTG
1381 ACCACCCACA TCCGGGAGCG TGAGGGTCGC ACCAAGGAGC AGGTTATGCT CCTCATCGAT
1441 ATTGAGCTGG CGTACATGAA TACCAATCAT GAGGACTTCA TAGGCTTTGC CAATGCTCAG
1501 CAGAGGAGCA ACCAGATGAA CAAGAAGAAG GCTTCAGGGA ACCAGGATGA GATTCTGGTC
1561 ATCCGGAAGG GCTGGCTGAC CATCAACAAT ATTGGCATCA TGAAGGGGGG CTCCAAGGAG
1621 TACTGGTTTG TCCTGACCGC TGAGAATCTG TCCTGGTACA AGGATGACGA GGAGAAAGAG
1681 AAGAAATACA TGCTCTCCGT GGACAATCTG AAGCTACGGG ACGTGGAGAA AGGTTTCATG
1741 TCAAGCAAGC ACATCTTTGC CCTCTTTAAC ACTGAGCAGA GGAATGTCTA CAAGGATTAT
1801 CGGCAGCTGG AACTGGCCTG TGAGACGCAA GAGGAGGTGG ATAGCTGGAA GGCCTCTTTC
1861 CTGCGGGCTG GCGTATATCC TGAACGCGTT GGGGACAAGG AGAAAGCCAG CGAAACAGAG
1921 GAGAATGGCT CAGACAGCTT CATGCACTCC ATGGACCCAC AGCTAGAGCG GCAGGTGGAG
1981 ACCATCCGGA ACCTGGTAGA CTCATACATG GCCATCGTGA ACAAGACCGT GCGTGACCTC
2041 ATGCCGAAGA CCATCATGCA CCTCATGATC AACAATACGA AGGAATTCAT CTTCTCGGAG
2101 CTGCTCGCCA ACCTGTACTC GTGCGGGGAC CAGAACACAC TGATGGAGGA GTCGGCGGAG
2161 CAGGCGCAAC GGCGCGACGA GATGCTGCGC ATGTACCACG CACTGAAGGA GGCGCTCAGC
2221 ATCATCGGCG ATATCAACAC GACCACCGTC AGCACGCCCA TGCCCCCGCC CGTGGACGAC
2281 TCCTGGCTGC AGGTGCAGAG CGTACCGGCC GGACGCAGGT CACCCACGTC CAGCCCACG
2341 CCGCAGCGCC GAGCCCCGC CGTGCCCCCA GCCCGGCCCG GGTCGCGGGG CCCTGCTCCT
2401 GGGCCTCCGC CTGCTGGGTC CGCCCTGGGG GGGCGCCCC CCGTGCCCTC CAGGCCGGGG
2461 GCTTCCCCTG ACCCCTTCGG TCCTCCCCCC CAGGTGCCCT CGCGCCCCAA CCGCGCCCCG
2521 CCCGGGGTCC CCAGCCGATC GGGTCAGGCA AGTCCGTCCC GTCCTGAGAG CCCCAGGCCC
2581 CCCTTCGACC TCTAA (SEQ ID NO:1)
```

Figure 2.

```
  1 MGNRGMEDLI PLVNRLQDAF SAIGQNADLD LPQIAVVGGQ SAGKSSVLEN FVGRDFLPRG
 61 SGIVTRRPLV LQLVNATTEY AEFLHCKGKK FTDFEEVRLE IEAETDRVTG TNKGISPVPI
121 NLRVYSPQVL NLTLVDLPGM TKVPVGDQPP DIEFQIRDML MQFVTKENCL ILAVSPANSD
181 LANSDALKVA KEVDPQGQRT IGVITKLDLM DEGTDARDVL ENKLLPLRRG YIGVVNRSQK
241 DIDGKKDISA ALAAERKFFL SHPSYRHLAD RMGTPYLQKV LNQQLTNHIR DTLPGLRNRL
301 QSQLLSIEKE VEEYKNFRPD DPARKTKALL QMVQQFAVDF EKRIEGSGDQ IDTYELSGGA
361 RINRIFHERF PFELVKMEFD EKELRREISY AIKNIHGIRT GLFTPDMAFE TIVKKQVKKI
421 REPCLKCVDM VISELISTVR QCTKKLQQYP RLREEMERIV TTHIREREGR TKEQVMLLID
481 IELAYMNTNH EDFIGFANAQ QRSNQMNKKK ASGNQDEILV IRKGWLTINN IGIMKGGSKE
541 YWFVLTAENL SWYKDDEEKE KKYMLSVDNL KLRDVEKGFM SSKHIFALFN TEQRNVYKDY
601 RQLELACETQ EEVDSWKASF LRAGVYPERV GDKEKASETE ENGSDSFMHS MDPQLERQVE
661 TIRNLVDSYM AIVNKTVRDL MPKTIMHLMI NNTKEFIFSE LLANLYSCGD QNTLMEESAE
721 QAQRRDEMLR MYHALKEALS IIGDINTTTV STPMPPPVDD SWLQVQSVPA GRRSPTSSPT
781 PQRRAPAVPP ARPGSRGPAP GPPPAGSALG GAPPVPSRPG ASPDPFGPPP QVPSRPNRAP
841 PGVPSRSGQA SPSRPESPRP PFDL (SEQ ID NO:2)
```

Figure 3.

```
Dog DNM1      241 DIDGKKDISA ALAAERKFFL SHPSYRHLAD (SEQ ID NO:3)
Dog DNM1(EIC)     DIDGKKDISA ALAAEKFFL  SHPSYRHLAD (SEQ ID NO:4)
Human DNM1        DIDGKKDITA ALAAERKFFL SHPSYRHLAD (SEQ ID NO:5)
Mouse DNM1        DIDGKKDITA ALAAERKFFL SHPSYRHLAD (SEQ ID NO:126)
Bovine DNM1       DIDGKKDITA ALAAERKFFL SHPSYRHLAD (SEQ ID NO:127)
Chicken           DIDGKKDIQA ALAAERKFFL SHPAYRHMAD (SEQ ID NO:6)
Danio rerio       DIDGRKDIRA ALAAERKFFL SHPSYRHMAE (SEQ ID NO:7)

Drosophila        DIEGRKDIHQ ALAAERKFFL SHPSYRHMAD (SEQ ID NO:8)
C elegans         DIVGRKDIRA ALDAERKFFI SHPSYRHMAD (SEQ ID NO:9)

Dog DNM1      241 DIDGKKDISA ALAAERKFFL SHPSYRHLAD (SEQ ID NO:3)
Human DNM2        DIEGKKDIRA ALAAERKFFL SHPAYRHMAD (SEQ ID NO:10)
Human DNM3        DIDGKKDIKA AMLAERKFFL SHPAYRHIAD (SEQ ID NO:11)
Mouse DNM2        DIEGKKDIRA ALAAERKFFL SHPAYRHMAD (SEQ ID NO:124)
Mouse DNM3        DIDGKKDIKA AMLAERKFFL SHPAYRHIAD (SEQ ID NO:125)
```

Figure 5A.

```
   1 ATGGGCAACC GCGGCATGGA GGATCTCATC CCGCTAGTCA ACCGGCTGCA GGACGCCTTC   60
  61 TCCGCTATCG GCCAGAACGC GGACCTCGAC CTACCGCAGA TCGCGGTGGT GGGCGGCCAG  120
 121 AGCGCCGGCA AGAGCTCGGT GCTCGAGAAT TTCGTAGGCA GGGACTTCCT GCCCCGAGGG  180
 181 TCAGGCATTG TCACCCGACG GCCCCTGGTC CTGCAGCTGG TCAATGCCAC CACAGAATAT  240
 241 GCCGAATTCC TGCACTGCAA GGGGAAGAAA TTCACTGACT TCGAGGAGGT ACGCCTGGAG  300
 301 ATCGAGGCTG AGACCGACCG GGTCACTGGC ACCAACAAGG GCATCTCGCC GGTGCCCATC  360
 361 AACCTCCGCG TCTACTCGCC TCAGGTCCTG AATCTGACAC TGGTGGACCT ACCCGGAATG  420
 421 ACCAAGGTCC CAGTGGGGGA CCAACCTCCT GACATCGAGT TCCAGATCCG GGACATGCTT  480
 481 ATGCAGTTCG TCACCAAAGA GAACTGCCTC ATCCTGGCTG TGTCCCCCGC CAACTCCGAC  540
 541 CTGGCCAACT CTGATGCTCT CAAGGTTGCC AAGGAGGTGG ACCCCCAGGG TCAGCGCACC  600
 601 ATGGGGTCA TCACCAAGCT AGATCTGATG GAGGAGGGCA CAGATGCCCG AGATGTGCTA  660
 661 GAGAATAAGC TCCTTCCCCT GCGCAGAGGC TACATAGGGG TGGTAAACCG AAGCCAGAAG  720
 721 GACATTGATG GCAAGAAGGA CATCTCAGCT GCCTTGGCG CTGAACCAA GTTCTTTCTC  780
 781 TCCCACCCAT CCTACCGCCA CTTGGCGGAC CGCATGGGCA CACCCTACCT ACAGAAGGTC  840
 841 CTCAACCAGC AACTGACCAA CCACATCCGG GACACACTGC CGGGGCTCCG GAACAGGCTG  900
 901 CAGAGCCAGC TACTGTCCAT TGAGAAGGAG GTGGAGGAGT ACAAGAACTT CCGACCTGAT  960
 961 GACCCAGCAC GCAAGACCAA GGCCCTGCTG CAGATGGTCC AGCAGTTTGC TGTGGACTTT 1020
1021 GAGAAGCGCA TTGAGGGCTC CGGGGACCAG ATTGACACCT ATGAACTGTC AGGGGGAGCC 1080
1081 CGCATCAACC GGATCTTCCA TGAGCGCTTC CCCTTTGAGC TAGTCAAGAT GGAGTTTGAT 1140
1141 GAGAAGGAGC TCCGGAGAGA GATCAGCTAC GCCATCAAGA ACATCCATGG CATTAGAACG 1200
1201 GGGCTCTTTA CCCCAGACAT GGCTTTTGAG ACCATTGTGA AAAAGCAGGT GAAGAAGATC 1260
1261 CGAGAACCGT GTCTCAAGTG TGTGGACATG GTTATCTCGG AACTAATCAG CACGGTTAGA 1320
1321 CAGTGCACCA AGAAGCTGCA GCAGTACCCC CGGCTGCGGG AGGAGATGGA GCGCATCGTG 1380
1381 ACCACCCACA TCCGGGAGCG TGAGGGTCGC ACCAAGGAGC AGGTTATGCT CCTCATCGAT 1440
1441 ATTGAGCTGG CGTACATGAA TACCAATCAT GAGGACTTCA TAGGCTTTGC CAATGCTCAG 1500
1501 CAGAGGAGCA ACCAGATGAA CAAGAAGAAG GCTTCAGGGA ACCAGGATGA GATTCTGGTC 1560
1561 ATCCGGAAGG GCTGGCTGAC CATCAACAAT ATTGGCATCA TGAAGGGGGG CTCCAAGGAG 1620
1621 TACTGGTTTG TCCTGACCGC TGAGAATCTG TCCTGGTACA AGGATGACGA GGAGAAAGAG 1680
1681 AAGAAATACA TGCTCTCCGT GGACAATCTG AAGCTACGGG ACGTGGAGAA AGGTTTCATG 1740
1741 TCAAGCAAGC ACATCTTTGC CCTCTTTAAC ACTGAGCAGA GGAATGTCTA CAAGGATTAT 1800
1801 CGGCAGCTGG AACTGGCCTG TGAGAC CAA GAGGAGGTGG ATAGCTGGAA GGCCTCTTTC 1860
1861 CTGCGGGCTG GCGTATATCC TGAACGCGTT GGGGACAAGG AGAAAGCCAG CGAAACAGAG 1920
1921 GAGAATGGCT CAGACAGCTT CATGCACTCC ATGGACCCAC AGCTAGAGCG GCAGGTGGAG 1980
1981 ACCATCCGGA ACCTGGTAGA CTCATACATG GCCATCGTGA ACAAGACCGT GCGTGACCTC 2040
2041 ATGCCGAAGA CCATCATGCA CCTCATGATC AACAATACGA AGGAATTCAT CTTCTCGGAG 2100
2101 CTGCTCGCCA ACCTGTACTC GTGCGGGGAC CAGAACCAC TGATGGAGGA GTCGGCGGAG 2160
2161 CAGGCGCAAC GGCGCGACGA GATGCTGCGC ATGTACCACG CACTGAAGGA GGCGCTCAGC 2220
2221 ATCATCGGCG ATATCAACAC GACCACCGTC AGCACGCCCA TGCCCCCGCC CGTGGACGAC 2280
2281 TCCTGGCTGC AGGTGCAGAG CGTACCGGCC GGACGCAGGT CACCCACGTC CAGCCCCACG 2340
2341 CCGCAGCGCC GAGCCCCCGC CGTGCCCCCA GCCCGGCCCG GTCGCGGGG CCCTGCTCCT 2400
2401 GGGCCTCCGC CTGCTGGGTC CGCCCTGGGG GGGCGCCCC CCGTGCCCTC CAGGCCGGGG 2460
2461 GCTTCCCCTG ACCCCTTCGG TCCTCCCCCC CAGGTGCCCT CGCGCCCCAA CCGCGCCCCG 2520
2521 CCCGGGGTCC CCAGGTGA    2538 (SEQ ID NO:12)
```

Figure 5B.

```
  1 MGNRGMEDLI PLVNRLQDAF SAIGQNADLD LPQIAVVGGQ SAGKSSVLEN FVGRDFLPRG   60
 61 SGIVTRRPLV LQLVNATTEY AEFLHCKGKK FTDFEEVRLE IEAETDRVTG TNKGISPVPI  120
121 NLRVYSPQVL NLTLVDLPGM TKVPVGDQPP DIEFQIRDML MQFVTKENCL ILAVSPANSD  180
181 LANSDALKVA KEVDPQGQRT GVITKLDLM EGTDARDVL ENKLLPLRRG YIGVVNRSQK  240
241 DIDGKKDISA AL AE KFFL SHPSYRHLAD RMGTPYLQKV LNQQLTNHIR DTLPGLRNRL  300
301 QSQLLSIEKE VEEYKNFRPD DPARKTKALL QMVQQFAVDF EKRIEGSGDQ IDTYELSGGA  360
361 RINRIFHERF PFELVKMEFD EKELRREISY AIKNIHGIRT GLFTPDMAFE TIVKKQVKKI  420
421 REPCLKCVDM VISELISTVR QCTKKLQQYP RLREEMERIV TTHIREREGR TKEQVMLLID  480
481 IELAYMNTNH EDFIGFANAQ QRSNQMNKKK ASGNQDEILV IRKGWLTINN IGIMKGGSKE  540
541 YWFVLTAENL SWYKDDEEKE KKYMLSVDNL KLRDVEKGFM SSKHIFALFN TEQRNVYKDY  600
601 RQLELACE Q EEVDSWKASF LRAGVYPERV GDKEKASETE ENGSDSFMHS MDPQLERQVE  660
661 TIRNLVDSYM AIVNKTVRDL MPKTIMHLMI NNTKEFIFSE LLANLYSCGD QNTLMEESAE  720
721 QAQRRDEMLR MYHALKEALS IIGDINTTTV STPMPPPVDD SWLQVQSVPA GRRSPTSSPT  780
781 PQRRAPAVPP ARPGSRGPAP GPPPAGSALG GAPPVPSRPG ASPDPFGPPP QVPSRPNRAP  840
841 PGVPR 845 (SEQ ID NO:13)
```

| Primer Pair | Forward Primer | Reverse Primer | Product Size | Product Sequence |
|---|---|---|---|---|
| Exon 1 | caatcccataatgcacag SEQ ID NO: 36 | acgacgtdgtggacaag SEQ ID NO: 37 | 599 | ggggccgcgcgcaggcactcggagcgcggdgcagcagaggagccgagcggaaccggaccggagccga gccggccggatcgcagccgcgggggcccgccgagcgATGGGCAACCGCGCGGCATGGAGGATCTCA TCCCGCTAGTCAACCGGCTGCAGAGACGCCTTTCTCCGCTATCGGCCAGAACGCGGACC TCGACCTACCGCACAGATGCGGTGGTGGGCGGCCAGAGCGCCGGCAAGAGCTCGGTG CTCGAGAATTTCGTAGGCAGgtaggagcgcgcgcccgagcgcgaactgcccccgccgggtccggc ctcgccccagcccgagcgccgcgcgccgcgatctgcagccctggcgctgcccccggaccgcgccctctccagcc agaggagggccccc (SEQ ID NO: 38) |
| Exon 2 | ttctcagctgccatctdcc SEQ ID NO: 39 | gaagagtgggggaggtaag SEQ ID NO: 40 | 520 | taaggtgtggtgggcactttggagagagttgaactccagtgrcaggatgtgtgccccagaacacaggagcccattcagg ccttgactcattgctactctcadcccaactcattcagGGACTTCCTGCCCCGAGGGTCAGGCATTGTCA CCCGACGGCGCCCTGGTCCTGCAGCTCCTGCAGCTCGGTCAATGCCACCACAGtatgcgtctcggacagca ctgaccccggcgctctcagcgtccccaccttatcccaaggagaggtdggcctagcgcgtgaacttgcttgctctaggacttggg cactgattcccctctcggacagtggggataaaatgcataacgaagacatgcgttgttggggaggagtg (SEQ ID NO: 41) |
| Exon 3 | aaggagaggtctggcctagc SEQ ID NO: 42 | ctgggggcggatctaagac SEQ ID NO: 43 | 452 | aggagaggtctggcctagccgcdgaacttgctctagaggacttggcttgctcttcdaggacttgctgcacdgattccccttcggacagtgggataaaatgcat aacgaagaacatggcgtttgtgggaggagtggggagagaaggcagtgttcgggtgtgtggtgtdatttccagggaagat ggaacctaggtgggttgggttagaatgctacccctccccacdcttcccacgtccccdtcttcggacagAATATGCCGAA TTCCTGCACTGCAAGGGGAAGAAATTCACTGACTTCGAGAGGAGTACGCCTGGAGATC GAGGCTGAGACGACCCGGGTCACTGGCACGCAACAAGGCATCTCGCCGGTGCCCATC AACCCTCCGCGTCTACTCCGCCCCTCAGgtgaggagtcgtgtcccgccccaggcctcggctcccgttagat ccgcccccag (SEQ ID NO: 44) |
| Exon 4 | ccctctgccaccctgtc SEQ ID NO: 45 | ctgcccttaggaacctaccc SEQ ID NO: 46 | 243 | ccctctgccactgtccagTCCTGAATCTCTGACACTGGTCGACCTACCCGGAATGACCAAGGTC CCAGTGGGGACCAACCTCCTTGACATGAAGTTCCAGATTCCGGGACATCCAGCTTATGCAGT TCGTCACCAAAGAGAACTTGCCTCATCCTGATCGTGTGTCCCCCGCCAACTCCGACCTGGC CAACTCTGATGCTCTCAAGGTTGCCAAGGAGGTTGGACCCCCAGGtaggttcctaagggcag (SEQ ID NO: 47) |

Figure 7B.

| Polymorphisms and Comments | Predicted Splice Site Sequences | Exon | Predicted Exon Sequence |
|---|---|---|---|
| Two possible inframe start codons exist | ——GT | 1 | ATGGGCAACCGCGGCATGGAGGATCTCATCCCGCTAGTCAACCGGCTGCAGGACG CCTTCTCCGCTATCGGCCAGAACGCGGACCTCGACCTACCGCAGATCGCGGTGGTG GGGGCCAGAGCGCCGCGGCAGCTCGGTGCTGCTCGAGAATTTCGTAGGCAG (SEQ ID NO: 48) |
| Intron 1 SNP1, 2 affected dogs are A/A, 1 unaffected dog is G/G, genome assembly is G/G; Intron SNP 2, 2 affected dogs and 1 unaffected dog are G/G, and genome assembly is C/C | AG——GT | 2 | GGACTTCCTGCCCCGAGGGTCAGGCATTGTCACCGACGGCCCCTGGTCCTGCAG CTGGTCAATGCCACCACAG (SEQ ID NO: 49) |
|  | AG——GT | 3 | AATATGCCGAATTCCTGCACTGCAAGGGGAAGAAATTCACTGACTTCGAGGAGGTA CGCCTGGAGATCGAGGCTGAGACGCGGTCACTGGCACCAACAAGGGCATCT CGCCGGTGCCCATCAACCTCCGCGTCTACTCGCCCTCAGG (SEQ ID NO: 50) |
|  | AG——GT | 4 | TCCTGAATCTGACACTGGTGGACCTACCCGGAATGACCAAGGTCCCAGTGGGGAC CAACCTCCTGACATCGAGTTCCAGATCCGGGACATGCTTATGCAGTTCGTCACCAAA GAGAACTGCCTCATCCTGGCTGTGTCCCGCCAACTCCGACCTGGCCAACTCTGA TGCTCTCAAGGTTGCCAAGGAGGTGGACCCCCAGG (SEQ ID NO: 51) |

Figure 7C.

| Primer Pair | Forward Primer | Reverse Primer | Product Size | Product Sequence |
|---|---|---|---|---|
| Exons 5 & 6 | aatgaggctgg agagcagag SEQ ID NO: 52 | tgaggacact aaccctgttg SEQ ID NO: 53 | 581 | gagagcagaggcaggtagtgggtgaggaggagggtgtgggtaggagagatgtgggaagcaggtggagtggaagtgcatgtggtctcctt gtgaggagaagcatgtcagatgtggaccttatctctgctgtccctagGTCAGCGCACCATYGGGGTCAT CACCAAGCTAGATCTGATGAYGAGGGCACAGATGCCCGAGATGTGCTAGAGAATA AGCTCCTTCCCCTGCGCAGAGgtaggtaggctctcgaccactcacctgcctttcaacccaccctgtgc gaggctggttgcccctgacttggccccttcacagGCTACATAGGGGTGGTAAACCGAAGCCAGAA GGACATTGATGGCAAGAAGGACATCTCAGCTGCCTTGGCYGCTGAACKCAAGTTCTT TCTCCCACCATCCTACCGCCACTTGGGGACCGCATGGGCACACCCTACCTAC AGAAGGTCCTCAACCAGgtaaggaactcaggcctgggaagcagcgtgggggacag SEQ ID NO: 54 |
| Exon 7,8,9 | ctgtgggcatc ccatttg SEQ ID NO: 55 | gcggctcactt tatcactcc SEQ ID NO: 56 | 815 | tccgctccctccccctcccctcagCAACTGACCAACCACCATCCGGGACACACTGCCGGGGCTCCG GAACAGGCTGCAGAGCCCAGCTACTGTCCATTGAGAAGGAGGTGGAGAGTACAAGA ACTTCCGACCTGATGACCCAGCACGCAAGACCAAGGCCCTGCTGCAgtgaggcccgcccc aactcctgacaccccagacgactgagctgccctctgcaccgggctctctcaggggctcctgcacaag gctgctgcagccccctcacgccatccaatctctccatcccccagGATGGTCACCTATGAACTGTCAGGG GGAGCCCGCATCAACCGGATCTTCCATGAGCGCTTCCCCTTTGAGCTAGTCAAGgtag gacagtccccagatgggcagagtggggagcttaggactaggaataccccacctccctccaggacttccacatgaacctttgctgac ctggtgccgataggagtgggggcctgtctggccttggccttcagggaggcaggaaggcctgaccagctgacctgcctttgctdctgcac agATGGAGTTTGATGAAGAGGAGCTCCGGAGAGAGATCAGCTACGCCATCAAGAACA TCCATGGCATTAGgcacgtatttgggaccgggggaaggggctgagcctg SEQ ID NO: 57 |

Figure 7D.

| Polymorphisms and Comments | Predicted Splice Site Sequences | Exon | Predicted Exon Sequence |
|---|---|---|---|
| Exon 5 SNP 1, 2 affected dogs are T/T, 1 unaffected is C/T, genome assembly is T/T; Exon 5 SNP 2, 2 affected dogs are C/C, 1 unaffected dogs is C/T, genome assembly is C/C; Exon 6 SNP 1, 12 affected dogs are C/C, one unaffected dog is C/T, 3 unaffected dogs are C/C, 8 unaffected dogs are C/T, genome assembly is C/C; Exon 6 SNP 2, 12 affected dogs are T/T, 6 unaffected dogs are G/G, 6 unaffected dogs are G/T, genome assembly is G/T; Exon 6 SNP 3, genome assembly is G/G (EIC mutation); Intron 6 SNP1, 12 affected dogs are C/C, 3 unaffected dogs are C/C, 1 unaffected dogs is T/T, 8 unaffected dogs are C/T, genome assembly is C/C | AG-------GT | 5 | GTCAGCGCACCATYGGGGTCATCACCAAGCTAGATCTGATGGAYGAGGGCACAGAT GCCCGAGATGTGCTAGAGAATAAGCTCCTTCCCCTGCGCAGAG (SEQ ID NO: 58) |
|  | AG-------GT | 6 | GCTACATAGGGGTGGTAAACCCAAGCCAGAAGCCAGACATTGATGGCAAGAAGGACATC TCAGCTGCCTTGGCYGCYGATGGCAACACCCTACCTAGAAGCTCTTCTCTCCCACCCATCCTCTACCGCCAC TTGGCGGACCGCATGGGCACACCCTACCTAGAAGTCTCAACCAG (SEQ ID NO: 59) |
| Intron 7 SNP just 5' to start of exon 8; Intron 8 SNP, 2 affected dogs are G/G, 1 unaffected dog is G/G, genome assembly is C/C | AG-------GT | 7 | CAACTGACCAACCACATCCGGGACACACTGCCGGGGCTCCCGAAACAGGCTGCAGA GCCAGCTACTGTCCATTGAGAAGGAGGTGGAGGAGTACAAGAACTTCCGACCTGAT GACCCAGCACGCAAGACCAAGGCCCTGCTGCA (SEQ ID NO: 60) |
|  | AG-------GT | 8 | GATGGTCCAGCAGTTTGCTGTGGACTTTGAGAAGCGCATTGAGGGCTCCGGGGACC AGATTGACACCTATGAACTGTCAGGGGGAGCCCGCCATCAACCGGATCTTCCATGAG (SEQ ID NO: 61) |
| Non GT site (i.e., GC) is also present in human | AG-------GC | 9 | ATGGAGTTTGATGAAGGAGCTCCGGAGAGAGATCAGCTACGCCATCAAGAACAT CCATGGCATTAG (SEQ ID NO: 62) |

Figure 7E.

| Primer Pair | Forward Primer | Reverse Primer | Product Size | Product Sequence |
|---|---|---|---|---|
| Exon 10 | ataagcagac cttgcctgc SEQ ID NO: 63 | cttagagag gcccctgtc SEQ ID NO: 64 | 520 | gtcctcattagaatcctccgcccatttacagatgaggacactgaagccagagagggtaatagcgggaggaccca aggagaaatcaggggtcggtgggtgggctggctagaactcggttaggagctggctgtgacactgcccttctccgctc cgggcgttcagAACGGGGCTCTTTACCCCAGACATGGCTTTTGAGACACATTGTGAAAAAG CAGGTGAAGAAGATCCGAGAACCGTGTCTCAAGTGTGTGGACATGGTTATCTCGGA ACTAATCAGCACGGTTAGACAGTGCACCAAGAAGtaaccggtggccggccagcccccacc tctgtccccatcctgcactgctgccaggcgctcttttcccacaccccactgcctcctcggtagcatgtacagaccctgagcgg ggtggggggaggcaggccacccagacaaggggcctctctgaag (SEQ ID NO: 65) |
| Exon 11 | accctcgagttg tcatttgg SEQ ID NO: 66 | gggtatgaca gatgggatg SEQ ID NO: 67 | 549 | ggctggtgcctcagcttcctgggaccccaggcctctcccctcatccgggcttctgtgtgcctcccagccacgccc ctgatcccggattctgttgggtggggagggagctcccgcagtgccccctgtacgtggctctctccctccgcccctccc cagCTGCAGCAGTACCCCGGCTGCGGGAGGAGATGGAGCGCATCGTGACCACCCA CATCCGGGAGCGTGAGGGTCGACACCAAGGAGCAGgtgagtccacagccctcctgcccctggcc ctctccctcctccttccccatttgcctcttcgttgtctcccacgctttcggcctcacactctgctctctcttttttt.actggg ggaaaaaatttccaactaaaaataccccctggccacctcaatgaacggtcaatggttattaaacacatttccctggtg gggccccctcatcccatccg (SEQ ID NO: 68) |
| Exon 12 | tttcttccagcctt tcatgc SEQ ID NO: 69 | cagctccaagc caaagagtg c SEQ ID NO: 70 | 700 | acctgcatatyctcaaagGTTATGCTCCTCATCGATATTGAGCTGGCGTACATGAATACCAAT CATGAGGACTTCATAGGCCTTTGCCAAgtgagtgctccctaggctaagaagtgacacctctagtgtgtgtgt gtgtgtgt:::::aggaaccaggccctgtgggttaaccct:ctgggtctggtgcccactgacgcagtgcattgaagctaggcctc ttgagaggagaagttctgagactcttctcttcttctttaggtgctcagcagaggaacagatgaacaagaagaaggctt cagggaaccaggtgagtgaaccccagtgcccagcggaggggttgagggtgccggatggacgccaagctctgagagc ccctccccccgaggggaagggtctcacagggcagggatc (SEQ ID NO: 71) |
| Exon 13 & 14 | ttaaccctctgg gtctgglg SEQ ID NO: 72 | ctgtgtatgtgc aagcagctc SEQ ID NO: 73 | 485 | ttttaaccctctggtctggtgccactgagcagtggcactggcctaggctttgagaggagaagttctgagactcttcctttctct tcttcttagTGCTCAGCAGAGGAGGAGCAACCAGATGAACAAGAAGAAGGCTTCAGGGAACCA Ggtgagtgaaccccagtgcccagcggagggagggtgccggatggacgccaagctcgaagagccccctccccc gaggggaagggtccaaagggcccaggaatctatcagctgccccaagcctcccactgcctgcctaaccctctctc ctctctcccgatgcttcgtggttgctatggttaccttctgacGATGAGATTCTGgtgagtaccaggactggggctctt ggcttgtatgccgaaggggaggaggagagggaccattagtagtggggatgccca (SEQ ID NO: 74) |

Figure 7F.

| Polymorphisms and Comments | Predicted Splice Site Sequences | Exon | Predicted Exon Sequence |
|---|---|---|---|
| Intron 10 SNP, 2 affected dogs are G/G, 1 unaffected dog is G/A, genome assembly is G/G | AG------GT | 10 | AACGGGGCTCTTTACCCCAGACATGGCTTTGAGACCATTGTGAAAAAGCAGGTGAAGAAGATCCGAGAACCGTGTCTCAAGTGTGTGGACATGGTTATCTCGGAACTAATCAGCACGGTTAGACAGTGCACCAAGAAG (SEQ ID NO: 75) |
| Intron 11 SNP1, 2 affected dogs are C/C, one unaffected dog is C/T, genome assembly is T/T; Intron 11 SNP2, indel in tttttttt sequence | AG------GT | 11 | CTGCAGCAGTACCCCCGGCTGCGGGAGGAGATGGAGCGCATCGTGACCACCCACATCCGGGAGCGTGAGGGTCGCACCAAGGAGCAG (SEQ ID NO: 76) |
| Intron 11 SNP, 2 affected dogs are C/C, 1 unaffected dog is C/C, genome assembly is T/T; GT repeat microsatellite in Intron 12 | AG------GT | 12 | GTTATGCTCCTCATCGATATTGAGCTGGCGTACATGAATACCAATCATGAGGACTTCATAGGCTTTGCCAA (SEQ ID NO: 77) |
| | AG------GT | 13 | TGCTCAGCAGAGGAGCAACCAGATGAACAAGAGAAGGCTTCAGGGAACCAG (SEQ ID NO: 78) |
| | AG------GT | 14 | GATGAGATTCTG (SEQ ID NO: 79) |

Figure 7G.

| Primer Pair | Forward Primer | Reverse Primer | Product Size | Product Sequence |
|---|---|---|---|---|
| Exon 15 | tgagctgacct atgccttcc SEQ ID NO: 80 | ttctctttccca cctggatg SEQ ID NO: 81 | 529 | acagggcaggtctggcccacacctccctgcccagccaggcttccaagagctggaggagggggtgggcttttgagtgtttctctt tgcctaccccatcctcagggagagtcctggcctctcccccactgacctcctgccctctcaccctccagGTCATCCGGAA GGGCTGGCTGACCATCAACAATATTGGCATCATGAAGGGGGGCTCCAAGGAGTACT GGTTTGTCCTGACCGCTGAGAATCTGTCCTGGTACAAGGATGACGAGgtgagtaaagggc cactggtcatcaaaggggtttggctggggccagattcaggctcagacactactccaagggcttggagtagattgggccaccca acaaacaaagttttttttttttttttt (SEQ ID NO: 82) |
| Exon 16 | actgggaacc agaggtgctc SEQ ID NO: 83 | gcagggtgtct taggcagag SEQ ID NO: 84 | 474 | gcagggggcatgggtgcccagaaacccagggcygccctggggctccagagccctgctccccactgccccaaacctccg catggaacactcttaggatatgaggcatggcaccgacctcacccatcgctcccacctctatccacagGAGAAAGAGA AGAAATACATGCTCTCCGTGGACAATCTGAAGCTACGGGACGTGGAGAAAGGTTTCA TGTCAAGCAAGCACATCTTTGCCCTCTTTAACACTGAGCAGAGgtgggtccccagactgcaag ccccaaaccaccttcctgagcagaaaggagagggacctgctccaagcccacagcgagagtcattccttgacaaatattc agtcaatcactggtaagcgcctgctctgcctaagacaccctgc (SEQ ID NO: 85) |
| Exon 17 | cttccaggcaa ggaaacaag SEQ ID NO: 86 | aggaattgcc atctgtggtc SEQ ID NO: 87 | 501 | cttccaggcaaggaaacaagctgggaggtgaggggacatgcccagggtcacacagctgggaaatgaggaagccagga ctgggcccaggtgtgatgtccccagtctgtgcatgccttaatcacctgggtgagtgggctccgagccttctccctcgccgc ctgcccacccttgcagGAATGTCTACAAGGATTATCGGCAGCTGGAACTGGCCTGTGAGACR CAAGAGGAGGTGGATAGCTGGAAGGCCTCTTTCCTGCGGGCTGGCCGTATATCCTGA ACGCGTTGGGgtgagtggaagggcagggaggggggcaagttacttctaataggggggccctgaatcactatcctcag cgatgccaagtcatgtcatcagggctcagaaatagcacagatcctcccccttaccdgtactggggtgggatcagagttaagcc (SEQ ID NO: 88) |
| Exon 18 | gtgtgtctgcttt ggctgtg SEQ ID NO: 89 | ccaccccctc ctgattc SEQ ID NO: 90 | 194 | ggtgtgtctgctttggctgtgctgctggtggcggcggcggtggtggtggcaatgctggtgtctggcctctatggctttggtgtggg cctcccagGACAAGGAGAAAgtgagtgtgccccctctcaccdtctkccaggtgtctccag (SEQ ID NO: 91) |
| Exon 19 | agttctccaggc accctc SEQ ID NO: 92 | atcccaaggg actggtctg SEQ ID NO: 93 | 367 | agttctccaggcaccctcaaggggctgagaccctgggagtggctggaacctggctacgagggcccagycrctctgatgccc tctattctcaacggcagGCCAGCGCGAAACAGAGGAGAATGGCTCAGACAGCTTCATGCACTCC ATGGACCCACAGCTAGAGCGGCAGGTGGAGACCATCCGGAACCTGGTAGACTCATA CATGGCCATCGTGAACAAGACCGTGCGTGACCTCATGCCGAAGACCATCATGCACC TCATGATCAACAATgtgggtgcaacacttygtgggcagtgggtgctctttgggaccagggaggga (SEQ ID NO: 94) |

Figure 7H.

| Polymorphisms and Comments | Predicted Splice Site Sequences | Exon | Predicted Exon Sequence |
|---|---|---|---|
| Intron 15 SNP, multiple indels in the 3" tttttttt sequence SEQ ID NO: 95 | AG------GT | 15 | GTCATCCGGAAGGGCTGGCTGACCATCAACAATATTGGCATCATGAAGGGGGGCTC CAAGGAGTACTGGTTTGTCCTGACCGCTGAGAATCTGTCCTGGTACAAGGATGACG AG (SEQ ID NO: 96) |
| Intron 15 SNP, 2 affected dogs are T/T, 1 unaffected dog is C/C, genome assembly is C/C | AG------GT | 16 | GAGAAAGAGAAGAAATACATGCTCTCCGTGGACAATCTGAAGCTACGGGACGTGGA GAAAGGTTTCATGTCAAGCAAGCACATCTTTGCCCTCTTTAACACTGAGCAGAG (SEQ ID NO: 97) |
| Exon 17 SNP, 2 affected dogs are A/A, 1 unaffected dog is G/G, genome assembly is A/A | AG------GT | 17 | GAATGTCTACAAGGATTATCGGCAGCTGGAACTGGCCTGTGAGACGCAAGAGGAGG TGGATAGCTGGAAGGCCTCTTTCCTGCGGGCTGGCGTATATCCTGAACGCGTTGGG (SEQ ID NO: 98) |
| Intron 17 SNP, 2 affected dogs are G/G, one unaffected dogs is A/G, genome assembly is G/G; Intron 18 SNP, 2 affected dogs are G/G, 1 unaffected dog is T/G, genome assembly is G/G | AG------GT | 18 | GACAAGGAGAAA (SEQ ID NO: 99) |
| Intron 18 SNP1, 2 affected dogs are C/C, 1 unaffected is T/T, genome assembly is C/C; Intron 18 SNP2, 2 affected dogs are G/G, one unaffected dog is A/A, genome assembly is G/G; Intron 19 SNP, 2 affected dogs are C/C, 1 unaffected dog is C/T, genome assembly is C/C | AG------GT | 19 | GCCAGCGAAACAGAGGAGAATGGCTCAGACAGCTTCATGCACTCCATGGACCCACA GCTAGAGCGGCAGGTGGAGACCATCCGGAACCTGGTAGACTCATACATGGCCATCG TGAACAAGACCGTGCGTGACCTCATGCCGAAGACCATCATGCACCTCATGATCAACA AT (SEQ ID NO: 100) |
| | | | |

Figure 7I.

| Primer Pair | Forward Primer | Reverse Primer | Product Size | Product Sequence |
|---|---|---|---|---|
| Exon 20 | aaagggcaag catggagac SEQ ID NO: 101 | tccgaagttcca gctccac SEQ ID NO: 102 | 600 | catggagacgggaaagcgggggagatctctgagtggcaaagccaggaccaccgagctcccagtccagcgcacggtccc ccaaggcggccagactggcacaggcgtcaggtcctagcccctcctctcttggcgcgcccgcagACGAAGGAATTC ATCTTCTCGGAGCTGCTCGCCAACCTGTACTCGTGCGGGGACCAGAACACACTGAT GGAGGAGTCGGCGGAGCAGGCGCAACGGCGCGACGAGATGCTGCGCATGTACCAC GCACTGAAGGAGGCGCTCAGCATCATCGGCGATATCAACACGACCACCGTCAGCAC GCCCATGCCCCCGCCCGTGGACGACTCCTGGCTGCAGGTGCAGAGCGTACCGGCC GGACGCAGgtaccagggccggcccccacggcccaaagccccaaccccggggccccgcgggaggtgggccggg accgggcagtggcgcgcccgcgtcaccggaacggctcccacctggagcaggggcggggcttagaga (SEQ ID NO: 103) |
| Exon 21 (5') | taacctccggg aacgagtag SEQ ID NO: 104 | tagaaagaagg gggcaggtg SEQ ID NO: 105 | 596 | ctggggcggggcctcaggatggggcggagctactcatctcctccctccttgtttccgcgcccctgtcgtccgcagGTCACC CACGTCCAGCCCCACGCCGCAGCGCCGAGCCCCCGCCGTGCCCCCAGCCCGGCCC GGGTCGCGGGGCCCTGCTCCTGGGCCTCCGCCTGCTGGGTCCGCCCTGGGGGG SEQ ID NO: 106 |
| Exon 21 (3') | ctcctccctcctt gttttcc SEQ ID NO: 107 | gtcctagcgccct ggatg SEQ ID NO: 108 | 353 | gGTCACCCACGTCCAGCCCCACGCCGCAGCGCCGAGCCCCCGCCGTGCCCCCAGC CCGGCCCGGGTCGCGGGGCCCTGCTCCTGGGCCTCCGCCTGCTGGGTCCGCCCTG GGGGGGGCGCCCCCCGTGCCCTCCAGGCCGGGGGCTTCCCCTGACCCCTTCGGTC CTCCCCCCAGGTGCCCTCGCGCCCCAACCGCGCCCCGCCCGGGGTCCCCAGGTG Agtaggggctgaatgcggcgggagagaccaccgggcgggcgta (SEQ ID NO: 109) |
| Exon 22 Alternate End | gccctgcctta ccagttc SEQ ID NO: 110 | gggagccactgt caagtcac SEQ ID NO: 111 | 206 | gccctgccttaccagttctcttcctccttctctccgttctctttttgcttctctccactgccagCCGATCGGGTCAGGCAA GTCCGTCCCGTCCTGAGAGCCCCAGGCCCCCCTTCGACCTCTAAccagatccctctattcctc ggagacctccctttccaagcctgcctggacggctgttctgtgacttgacagtggctccc (SEQ ID NO: 112) |

| | | | | |
|---|---|---|---|---|
| Exon 6 for genotyping | gtaggctctccg acccactc SEQ ID NO: 113 | tgaggacactaa cccctgttg SEQ ID NO: 114 | 337 | tagggagatgtgggaagcaggtggagtgcatgtggtctcccttgtgaggagagcatgtgcagatgtaggtgaccctctctgct gtcccctaggtcagcgcaccatcggggtcatcaccaagctagatctgatggatgagggcacagatgcccgagatgtgctag agaataagctcctccctgcgcagaggtaggtaggctctccgaccactccacctgccctcttcaccccacccctgtgcgag gctggttgcccctgacttcggccccctccacagGCTACATAGGGGTGGTAAACCGAAGCCAGAAGG ACATTGATGGCAAGAAGGACATCTCAGCTGCCTTGGCYGCTGAACGCAAGTTCTTTC TCTCCCACCCATCCTACCGCCACTTGGCGGACCGCATGGGCACACCCTACCTACAG AAGGTCCTCAACCAGgtaaggaactcaggcctggggaaagcagcgtgggacaggtatatttaaatgtgtttgtg aaggtga (SEQ ID NO: 115) |

Figure 7J.

| Polymorphisms and Comments | Predicted Splice Site Sequences | Exon | Predicted Exon Sequence |
|---|---|---|---|
| | AG———GT | 20 | ACGAAGGAATTCATCTTCTCGGAGCTGCTCGCCAACCTGTACTCGTGCGGGGACCA GAACACACTGATGGAGGAGTCGGCGGAGCAGGCGCAACGGCGCGACGAGATGCTG CGCATGTACCACGCACTGAAGGAGGCGCTCAGCATCATCGGCGATATCAACACGAC CACCGTCAGCACGCCCATGCCCCCGCCCGTGGACGACTCCTGGCTGCAGGTGCAG AGCGTACCGGCCGGACGCAG (SEQ ID NO: 116) |
| | AG——— | 21 | GTCACCCACGTCCAGCCCCACGCCGCAGCGCCGAGCCCCCGCCGTGCCCCAGCC CGGCCCGGGTCGCGGGGCCCTGCTCCTGGGCCTCCGCCTGCTGGGTCCGCCCTG GGGGGGCGCCCCCCGTGCCCTCCAGGCCGGGGGCTTCCCCTGACCCCTTCGGT CCTCCCCCCAGGTGCCCTCGCGCCCCAACCGCGCCCCGCCCGGGGTCCCCAGGT GA (SEQ ID NO: 117) |
| To make the long form, break exon 21 at the AG GTGA near the 3' end of the coding sequence, and splice to this Alt End seqeunce after its 5' ag. The longer transcript uses the GT from the short form as a splice site signal to connect with the Alt end coding sequence downstream from the ag. | AG——— | Alt End | CCGATCGGGTCAGGCAAGTCCGTCCCGTCCTGAGAGCCCCAGGCCCCCCTTCGAC CTCTAA (SEQ ID NO: 118) |
| Exon 6 SNP 1, unaffected is Y (C/T), Tasha is C; Exon 6 SNP 2, unaffected is G, affected is T (EIC mutation) | AG———GT | 6 | GCTACATAGGGGTGGTAAACCGAAGCCAGAAGGACATTGATGGCAAGAAGGACATC TCAGCTGCCTTGGCYGCTGAACGCAAGTTCTTTCTCTCCCACCCATCCTACCGCCAC TTGGCGGACCGCATGGGCACACCCTACCTACAGAAGGTCCTCAACCAG (SEQ ID NO: 119) |
| | | | |

Figure 9

| | | | | | |
|---|---|---|---|---|---|
| URM1 | 58,487 | bp: 58486128-58501133 | length: 15006 | Gene: ENSCAFG00000023618 | .48" |
| SLC27A4 | | bp: 58508896-58520185 | length: 11290 | Gene:ENSCAFG00000020063 | .36" |
| COQ4 | 58,527 | bp: 58527495-58537771 | length: 10277 | Gene: ENSCAFG00000020067 | 0.33 |
| TRUB2 | | bp: 58538202-58547593 | length: 9392 | Gene: ENSCAFG00000020068 | 0.3 |
| C9orf119 | 58,573 | bp: 58573597-58579355 | length: 5759 | Gene: ENSCAFG00000023381 | 0.18 |
| GOLGA2 | | bp: 58578944-58595033 | length: 16090 | Gene: ENSCAFG00000020072 | 0.52 |
| DNM1 | 58,596 | bp: 58599318-58642207 | length: 42890 | Gene: ENSCAFG00000020082 | 1.37 |
| CIZ1 | | bp: 58648241-58663023 | length: 14783 | Gene: ENSCAFG00000020086 | 0.47 |
| C9orf16 | | bp: 58664036-58667360 | length: 3325 | Gene: ENSCAFG00000020087 | 0.11 |
| LCN2 | | bp: 58672530-5867606 | length: 3539 | Gene: ENSCAFG00000020088 | 0.11 |
| LOC389791 | | bp: 58687589-58693005 | length: 5417 | Gene: ENSCAFG00000020089 | 0.17 |
| SLC25A25 | | bp: 58704336-58720909 | length: 16574 | Gene: ENSCAFG00000020091 | 0.53 |
| C9orf90 | | bp: 58739787-58742489 | length: 2703 | Gene: ENSCAFG00000020093 | 0.09 |
| LOC72972 | 58,779 | | | | |
| FAM102A | | bp: 58794037-58825063 | length: 31027 | Gene: ENSCAFG00000020094 | 0.99 |
| DPM2 | | bp: 58830285-58832145 | length: 1861 | Gene: ENSCAFG00000020095 | 0.06 |
| PIP5KL1 | | bp: 58835218-58843177 | length: 7960 | Gene: ENSCAFG00000020098 | 0.25 |
| ST6GALNAC4 | | bp: 58848210-58857484 | length: 9275 | Gene: ENSCAFG0000002010 | 0.3 |
| LOC609143 | | | | | |
| ST6GALN | 58,866 | bp: 58864573-58876517 | length: 11945 | Gene: ENSCAFG00000020103 | 0.38 |
| | | bp: 58887655-58892426 | length: 4772 | Gene: ENSCAFG00000020105 | 0.15 |
| ENG | 58,900 | bp: 58911399-58933429 | length: 22031 | Gene: ENSCAFG0000002010 | 0.7 |
| FPGS | | bp: 58934901-58943393 | length: 8493 | Gene: ENSCAFG00000020111 | 0.27 |
| CDK9 | | bp: 58960192-58963681 | length: 3490 | Gene: ENSCAFG000000201 | 0.11 |
| SH2D3C | 58,967 | bp: 58970716-59000641 | length: 29926 | Gene: ENSCAFG00000020118 | 0.96 |

SEQUENCE LISTING

<160> NUMBER OF SEQ ID NOS: 128

<210> SEQ ID NO 1
<211> LENGTH: 2595
<212> TYPE: DNA
<213> ORGANISM: Canis lupis familiaris

<400> SEQUENCE: 1

```
atgggcaacc gcggcatgga ggatctcatc ccgctagtca accggctgca ggacgccttc      60
tccgctatcg gccagaacgc ggacctcgac ctaccgcaga tcgcggtggt gggcggccag     120
agcgccggca agagctcggt gctcgagaat ttcgtaggca gggacttcct gcccccgaggg    180 tcaggcattg tcacccgacg gccctggtc ctgcagctgg tcaatgccac cacagaatat      240
gccgaattcc tgcactgcaa ggggaagaaa ttcactgact tcgaggaggt acgcctggag     300
atcgaggctg agaccgaccg ggtcactggc accaacaagg gcatctcgcc ggtgcccatc     360
aacctccgcg tctactcgcc tcaggtcctg aatctgacac tggtggacct accggaatg      420 accaaggtcc cagtggggga ccaacctcct gacatcgagt tccagatccg ggacatgctt     480
atgcagttcg tcaccaaaga gaactgcctc atcctggctg tgtcccccgc caactccgac    540
ctggccaact ctgatgctct caaggttgcc aaggaggtgg accccaggg tcagcgcacc     600 atyggggtca tcaccaagct agatctgatg gaygagggca cagatgcccg agatgtgcta    660
gagaataagc tccttcccct gcgcagaggc tacataggg tggtaaaccg aagccagaag      720
gacattgatg gcaagaagga catctcagct gccttggcyg ctgaacgcaa gttctttctc    780
tcccacccat cctaccgcca cttggcggac cgcatgggca caccctacct acagaaggtc     840
ctcaaccagc aactgaccaa ccacatccgg gacacactgc cggggctccg gaacaggctg     900
cagagccagc tactgtccat tgagaaggag gtggaggagt acaagaactt ccgacctgat     960
gacccagcac gcaagaccaa ggcccctgctg cagatggtcc agcagtttgc tgtggactttt    1020 gagaagcgca ttgagggctc cggggaccag attgacacct atgaactgtc aggggggagcc    1080 cgcatcaacc ggatcttcca tgagcgcttc ccctttgagc tagtcaagat ggagtttgat    1140
gagaaggagc tccggagaga gatcagctac gccatcaaga acatccatgg cattagaacg     1200
gggctcttta ccccagacat ggcttttgag accattgtga aaaagcaggt gaagaagatc    1260
cgagaaccgt gtctcaagtg tgtggacatg gttatctcgg aactaatcag cacggttaga    1320
cagtgcacca agaagctgca gcagtacccc cggctgcggg aggagatgga gcgcatcgtg    1380
accacccaca tccgggagcg tgagggtcgc accaaggagc aggttatgct cctcatcgat    1440
attgagctgg cgtacatgaa taccaatcat gaggacttca taggctttgc caatgctcag     1500
cagaggagca accagatgaa caagaagaag gcttcaggga accaggatga gattctggtc    1560
atccggaagg gctggctgac catcaacaat attggcatca tgaaggggggg ctccaaggag    1620 tactggtttg tcctgaccgc tgagaatctg tcctggtaca aggatgacga ggagaaagag    1680
```

```
aagaaataca tgctctccgt ggacaatctg aagctacggg acgtggagaa aggtttcatg     1740
tcaagcaagc acatctttgc cctctttaac actgagcaga ggaatgtcta caaggattat     1800
cggcagctgg aactggcctg tgagacgcaa gaggaggtgg atagctggaa ggcctctttc     1860
ctgcgggctg gcgtatatcc tgaacgcgtt ggggacaagg agaaagccag cgaaacagag     1920
gagaatggct cagacagctt catgcactcc atggacccac agctagagcg gcaggtggag     1980
accatccgga acctggtaga ctcatacatg gccatcgtga acaagaccgt gcgtgacctc     2040
atgccgaaga ccatcatgca cctcatgatc aacaatacga aggaattcat cttctcggag     2100
ctgctcgcca acctgtactc gtgcggggac cagaacacac tgatggagga gtcggcggag     2160
caggcgcaac ggcgcgacga gatgctgcgc atgtaccacg cactgaagga ggcgctcagc     2220
atcatcggcg atatcaacac gaccaccgtc agcacgccca tgccccccgcc cgtggacgac     2280 tcctggctgc aggtgcagag cgtaccggcc ggacgcaggt cacccacgtc agccccacg      2340 ccgcagcgcc gagcccccgc cgtgcccca gcccggcccg gtcgcgggg ccctgctcct       2400 gggcctccgc ctgctgggtc cgccctgggg ggggcgcccc ccgtgccctc caggccgggg     2460
gcttcccctg accccttcgg tcctcccccc caggtgccct cgcgcccaa ccgcgccccg      2520 cccggggtcc ccagccgatc gggtcaggca agtccgtccc gtcctgagag ccccaggccc     2580
cccttcgacc tctaa                                                      2595

<210> SEQ ID NO 2
<211> LENGTH: 864
<212> TYPE: PRT
<213> ORGANISM: Canis lupis familiaris

<400> SEQUENCE: 2

Met Gly Asn Arg Gly Met Glu Asp Leu Ile Pro Leu Val Asn Arg Leu
 1               5                  10                  15

Gln Asp Ala Phe Ser Ala Ile Gly Gln Asn Ala Asp Leu Asp Leu Pro
             20                  25                  30

Gln Ile Ala Val Val Gly Gly Gln Ser Ala Gly Lys Ser Ser Val Leu
         35                  40                  45

Glu Asn Phe Val Gly Arg Asp Phe Leu Pro Arg Gly Ser Gly Ile Val
     50                  55                  60

Thr Arg Arg Pro Leu Val Leu Gln Leu Val Asn Ala Thr Thr Glu Tyr
 65                  70                  75                  80

Ala Glu Phe Leu His Cys Lys Gly Lys Lys Phe Thr Asp Phe Glu Glu
                 85                  90                  95

Val Arg Leu Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro Gln
        115                 120                 125

Val Leu Asn Leu Thr Leu Val Asp Leu Pro Gly Met Thr Lys Val Pro
    130                 135                 140

Val Gly Asp Gln Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Lys Val Ala Lys Glu
            180                 185                 190

Val Asp Pro Gln Gly Gln Arg Thr Ile Gly Val Ile Thr Lys Leu Asp
        195                 200                 205
```

-continued

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Ser Ala Ala Leu Ala Ala Glu Arg
                245                 250                 255

Lys Phe Phe Leu Ser His Pro Ser Tyr Arg His Leu Ala Asp Arg Met
                260                 265                 270

Gly Thr Pro Tyr Leu Gln Lys Val Leu Asn Gln Gln Leu Thr Asn His
            275                 280                 285

Ile Arg Asp Thr Leu Pro Gly Leu Arg Asn Arg Leu Gln Ser Gln Leu
    290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
                325                 330                 335

Ala Val Asp Phe Glu Lys Arg Ile Glu Gly Ser Gly Asp Gln Ile Asp
                340                 345                 350

Thr Tyr Glu Leu Ser Gly Gly Ala Arg Ile Asn Arg Ile Phe His Glu
            355                 360                 365

Arg Phe Pro Phe Glu Leu Val Lys Met Glu Phe Asp Glu Lys Glu Leu
    370                 375                 380

Arg Arg Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Lys Gln
                405                 410                 415

Val Lys Lys Ile Arg Glu Pro Cys Leu Lys Cys Val Asp Met Val Ile
                420                 425                 430

Ser Glu Leu Ile Ser Thr Val Arg Gln Cys Thr Lys Lys Leu Gln Gln
            435                 440                 445

Tyr Pro Arg Leu Arg Glu Glu Met Glu Arg Ile Val Thr Thr His Ile
    450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
                485                 490                 495

Ala Asn Ala Gln Gln Arg Ser Asn Gln Met Asn Lys Lys Ala Ser
                500                 505                 510

Gly Asn Gln Asp Glu Ile Leu Val Ile Arg Lys Gly Trp Leu Thr Ile
            515                 520                 525

Asn Asn Ile Gly Ile Met Lys Gly Gly Ser Lys Glu Tyr Trp Phe Val
530                 535                 540

Leu Thr Ala Glu Asn Leu Ser Trp Tyr Lys Asp Asp Glu Glu Lys Glu
545                 550                 555                 560

Lys Lys Tyr Met Leu Ser Val Asp Asn Leu Lys Leu Arg Asp Val Glu
                565                 570                 575

Lys Gly Phe Met Ser Ser Lys His Ile Phe Ala Leu Phe Asn Thr Glu
                580                 585                 590

Gln Arg Asn Val Tyr Lys Asp Tyr Arg Gln Leu Glu Leu Ala Cys Glu
            595                 600                 605

Thr Gln Glu Glu Val Asp Ser Trp Lys Ala Ser Phe Leu Arg Ala Gly
    610                 615                 620

Val Tyr Pro Glu Arg Val Gly Asp Lys Glu Lys Ala Ser Glu Thr Glu
625                 630                 635                 640

```
Glu Asn Gly Ser Asp Ser Phe Met His Ser Met Asp Pro Gln Leu Glu
            645                 650                 655

Arg Gln Val Glu Thr Ile Arg Asn Leu Val Asp Ser Tyr Met Ala Ile
        660                 665                 670

Val Asn Lys Thr Val Arg Asp Leu Met Pro Lys Thr Ile Met His Leu
    675                 680                 685

Met Ile Asn Asn Thr Lys Glu Phe Ile Phe Ser Glu Leu Leu Ala Asn
690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asp Ile Asn Thr Thr Thr Val Ser Thr
            740                 745                 750

Pro Met Pro Pro Pro Val Asp Asp Ser Trp Leu Gln Val Gln Ser Val
        755                 760                 765

Pro Ala Gly Arg Arg Ser Pro Thr Ser Ser Pro Thr Pro Gln Arg Arg
    770                 775                 780

Ala Pro Ala Val Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
                805                 810                 815

Ser Arg Pro Gly Ala Ser Pro Asp Pro Phe Gly Pro Pro Gln Val
            820                 825                 830

Pro Ser Arg Pro Asn Arg Ala Pro Pro Gly Val Pro Ser Arg Ser Gly
        835                 840                 845

Gln Ala Ser Pro Ser Arg Pro Glu Ser Pro Arg Pro Pro Phe Asp Leu
    850                 855                 860

<210> SEQ ID NO 3
<211> LENGTH: 30
<212> TYPE: PRT
<213> ORGANISM: Canis lupis familiaris

<400> SEQUENCE: 3

Asp Ile Asp Gly Lys Lys Asp Ile Ser Ala Ala Leu Ala Ala Glu Arg
1               5                   10                  15

Lys Phe Phe Leu Ser His Pro Ser Tyr Arg His Leu Ala Asp
            20                  25                  30

<210> SEQ ID NO 4
<211> LENGTH: 30
<212> TYPE: PRT
<213> ORGANISM: Canis lupis familiaris

<400> SEQUENCE: 4

Asp Ile Asp Gly Lys Lys Asp Ile Ser Ala Ala Leu Ala Ala Glu Leu
1               5                   10                  15

Lys Phe Phe Leu Ser His Pro Ser Tyr Arg His Leu Ala Asp
            20                  25                  30

<210> SEQ ID NO 5
<211> LENGTH: 30
<212> TYPE: PRT
<213> ORGANISM: Homo sapiens

<400> SEQUENCE: 5

Asp Ile Asp Gly Lys Lys Asp Ile Thr Ala Ala Leu Ala Ala Glu Arg
```

```
                1               5                   10                  15
Lys Phe Phe Leu Ser His Pro Ser Tyr Arg His Leu Ala Asp
            20                  25                  30

<210> SEQ ID NO 6
<211> LENGTH: 30
<212> TYPE: PRT
<213> ORGANISM: Gallus gallus

<400> SEQUENCE: 6

Asp Ile Asp Gly Lys Lys Asp Ile Gln Ala Ala Leu Ala Ala Glu Arg
1               5                   10                  15

Lys Phe Phe Leu Ser His Pro Ala Tyr Arg His Met Ala Asp
            20                  25                  30

<210> SEQ ID NO 7
<211> LENGTH: 30
<212> TYPE: PRT
<213> ORGANISM: Danio rerio

<400> SEQUENCE: 7

Asp Ile Asp Gly Arg Lys Asp Ile Arg Ala Ala Leu Ala Ala Glu Arg
1               5                   10                  15

Lys Phe Phe Leu Ser His Pro Ser Tyr Arg His Met Ala Glu
            20                  25                  30

<210> SEQ ID NO 8
<211> LENGTH: 30
<212> TYPE: PRT
<213> ORGANISM: Drosophila melanogaster

<400> SEQUENCE: 8

Asp Ile Glu Gly Arg Lys Asp Ile His Gln Ala Leu Ala Ala Glu Arg
1               5                   10                  15

Lys Phe Phe Leu Ser His Pro Ser Tyr Arg His Met Ala Asp
            20                  25                  30

<210> SEQ ID NO 9
<211> LENGTH: 30
<212> TYPE: PRT
<213> ORGANISM: Caenorhabditis elegans

<400> SEQUENCE: 9

Asp Ile Val Gly Arg Lys Asp Ile Arg Ala Ala Leu Asp Ala Glu Arg
1               5                   10                  15

Lys Phe Phe Ile Ser His Pro Ser Tyr Arg His Met Ala Asp
            20                  25                  30

<210> SEQ ID NO 10
<211> LENGTH: 30
<212> TYPE: PRT
<213> ORGANISM: Homo sapiens

<400> SEQUENCE: 10

Asp Ile Glu Gly Lys Lys Asp Ile Arg Ala Ala Leu Ala Ala Glu Arg
1               5                   10                  15

Lys Phe Phe Leu Ser His Pro Ala Tyr Arg His Met Ala Asp
            20                  25                  30

<210> SEQ ID NO 11
<211> LENGTH: 30
<212> TYPE: PRT
<213> ORGANISM: Homo sapiens
```

<400> SEQUENCE: 11

Asp Ile Asp Gly Lys Lys Asp Ile Lys Ala Ala Met Leu Ala Glu Arg
1               5                   10                  15

Lys Phe Phe Leu Ser His Pro Ala Tyr Arg His Ile Ala Asp
            20                  25                  30

<210> SEQ ID NO 12
<211> LENGTH: 2538
<212> TYPE: DNA
<213> ORGANISM: Canis lupis familiaris

<400> SEQUENCE: 12

```
atgggcaacc gcggcatgga ggatctcatc ccgctagtca accggctgca ggacgccttc    60
tccgctatcg gccagaacgc ggacctcgac ctaccgcaga tcgcggtggt gggcggccag   120
agcgccggca agagctcggt gctcgagaat ttcgtaggca gggacttcct gccccgaggg   180
tcaggcattg tcacccgacg gcccctggtc ctgcagctgg tcaatgccac cacagaatat   240
gccgaattcc tgcactgcaa ggggaagaaa ttcactgact cgaggaggt acgcctggag    300
atcgaggctg agaccgaccg ggtcactggc accaacaagg gcatctcgcc ggtgcccatc   360
aacctccgcg tctactcgcc tcaggtcctg aatctgacac tggtggacct acccggaatg   420
accaaggtcc cagtgggga ccaacctcct gacatcgagt tccagatccg gacatgctt     480
atgcagttcg tcaccaaaga gaactgcctc atcctggctg tgtccccgc caactccgac    540
ctggccaact ctgatgctct caaggttgcc aaggaggtgg accccaggg tcagcgcacc    600
atygggtca tcaccaagct agatctgatg gaygagggca cagatgcccg agatgtgcta    660
gagaataagc tccttcccct gcgcagaggc tacataggg tggtaaaccg aagccagaag    720
gacattgatg gcaagaagga catctcagct gccttggcyg ctgaacgcaa gttctttctc   780
tcccacccat cctaccgcca cttggcggac cgcatgggca cccctacct acagaaggtc    840
ctcaaccagc aactgaccaa ccacatccgg gacacactgc cggggctccg gaacaggctg   900
cagagccagc tactgtccat gagaaggag gtggaggagt acaagaactt ccgacctgat    960
gacccagcac gcaagaccaa ggccctgctg cagatggtcc agcagtttgc tgtggacttt   1020
gagaagcgca ttgagggctc cggggaccag attgacacct atgaactgtc aggggagcc   1080
cgcatcaacc ggatcttcca tgagcgcttc ccctttgagc tagtcaagat ggagtttgat   1140
gagaaggagc tccggagaga gatcagctac gccatcaaga acatccatgg cattagaacg   1200
gggctcttta ccccagacat ggcttttgag accattgtga aaagcaggt gaagaagatc   1260
cgagaaccgt gtctcaagtg tgtggacatg gttatctcgg aactaatcag cacggttaga   1320
cagtgcacca agaagctgca gcagtacccc cggctgcggg aggagatgga gcgcatcgtg   1380
accacccaca tccgggagcg tgagggtcgc accaaggagc aggttatgct cctcatcgat   1440
attgagctgg cgtacatgaa taccaatcat gaggacttca taggctttgc caatgctcag   1500
cagaggagca accagatgaa caagaagaag gcttcaggga accaggatga gattctggtc   1560
atccggaagg gctggctgac catcaacaat attggcatca tgaagggggg ctccaaggag   1620
tactggtttg tcctgaccgc tgagaatctg tcctggtaca aggatgacga ggagaaagag   1680
aagaaataca tgctctccgt ggacaatctg aagctacggg acgtgagaa aggtttcatg    1740
tcaagcaagc acatctttgc cctctcttaac actgagcaga ggaatgtcta caaggattat   1800
cggcagctgg aactggcctg tgagacgcaa gaggaggtgg atagctggaa ggcctctttc   1860
ctgcgggctg gcgtatatcc tgaacgcgtt ggggacaagg agaaagccag cgaaacagag   1920
```

-continued

```
gagaatggct cagacagctt catgcactcc atggacccac agctagagcg gcaggtggag    1980
accatccgga acctggtaga ctcatacatg gccatcgtga acaagaccgt gcgtgacctc    2040
atgccgaaga ccatcatgca cctcatgatc aacaatacga aggaattcat cttctcggag    2100
ctgctcgcca acctgtactc gtgcggggac cagaacacac tgatggagga gtcggcggag    2160
caggcgcaac ggcgcgacga gatgctgcgc atgtaccacg cactgaagga ggcgctcagc    2220
atcatcggcg atatcaacac gaccaccgtc agcacgccca tgcccccgcc cgtggacgac    2280
tcctggctgc aggtgcagag cgtaccggcc ggacgcaggt cacccacgtc agccccacg     2340 ccgcagcgcc gagccccgc cgtgccccca gcccggcccg ggtcgcgggg ccctgctcct     2400
gggcctccgc ctgctgggtc cgccctgggg ggggcgcccc ccgtgccctc caggccgggg    2460
gcttcccctg accccttcgg tcctccccc caggtgccct cgcgcccaa ccgcgccccg      2520 cccggggtcc ccaggtga                                                  2538
```

<210> SEQ ID NO 13
<211> LENGTH: 845
<212> TYPE: PRT
<213> ORGANISM: Canis lupis familiaris

<400> SEQUENCE: 13

```
Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80

Ala Glu Phe Leu His Cys Lys Gly Lys Lys Phe Thr Asp Phe Glu Glu
                85                  90                  95

Val Arg Leu Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro Gln
        115                 120                 125

Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Lys Val Ala Lys Glu
            180                 185                 190

Val Asp Pro Gln Gly Gln Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Ser Ala Ala Leu Ala Ala Glu Arg
                245                 250                 255

Lys Phe Phe Leu Ser His Pro Ser Tyr Arg His Leu Ala Asp Arg Met
```

```
            260                 265                 270
Gly Thr Pro Tyr Leu Gln Lys Val Leu Asn Gln Gln Leu Thr Asn His
            275                 280                 285

Ile Arg Asp Thr Leu Pro Gly Leu Arg Asn Arg Leu Gln Ser Gln Leu
290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
            325                 330                 335

Ala Val Asp Phe Glu Lys Arg Ile Glu Gly Ser Gly Asp Gln Ile Asp
            340                 345                 350

Thr Tyr Glu Leu Ser Gly Gly Ala Arg Ile Asn Arg Ile Phe His Glu
            355                 360                 365

Arg Phe Pro Phe Glu Leu Val Lys Met Glu Phe Asp Glu Lys Glu Leu
            370                 375                 380

Arg Arg Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Lys Gln
            405                 410                 415

Val Lys Lys Ile Arg Glu Pro Cys Leu Lys Cys Val Asp Met Val Ile
            420                 425                 430

Ser Glu Leu Ile Ser Thr Val Arg Gln Cys Thr Lys Lys Leu Gln Gln
            435                 440                 445

Tyr Pro Arg Leu Arg Glu Glu Met Glu Arg Ile Val Thr Thr His Ile
            450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
            485                 490                 495

Ala Asn Ala Gln Gln Arg Ser Asn Gln Met Asn Lys Lys Lys Ala Ser
            500                 505                 510

Gly Asn Gln Asp Glu Ile Leu Val Ile Arg Lys Gly Trp Leu Thr Ile
            515                 520                 525

Asn Asn Ile Gly Ile Met Lys Gly Gly Ser Lys Glu Tyr Trp Phe Val
530                 535                 540

Leu Thr Ala Glu Asn Leu Ser Trp Tyr Lys Asp Asp Glu Glu Lys Glu
545                 550                 555                 560

Lys Lys Tyr Met Leu Ser Val Asp Asn Leu Lys Leu Arg Asp Val Glu
            565                 570                 575

Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
            595                 600                 605

Thr Gln Glu Glu Val Asp Ser Trp Lys Ala Ser Phe Leu Arg Ala Gly
            610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
            645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
            675                 680                 685
```

-continued

```
Met Ile Asn Asn Thr Lys Glu Phe Ile Phe Ser Glu Leu Leu Ala Asn
        690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asp Ile Asn Thr Thr Val Ser Thr
            740                 745                 750

Pro Met Pro Pro Val Asp Asp Ser Trp Leu Gln Val Gln Ser Val
        755                 760                 765

Pro Ala Gly Arg Arg Ser Pro Thr Ser Ser Pro Thr Pro Gln Arg Arg
    770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
                805                 810                 815

Ser Arg Pro Gly Ala Ser Pro Asp Pro Phe Gly Pro Pro Gln Val
            820                 825                 830

Pro Ser Arg Pro Asn Arg Ala Pro Pro Gly Val Pro Arg
        835                 840                 845

<210> SEQ ID NO 14
<211> LENGTH: 48
<212> TYPE: DNA
<213> ORGANISM: Canis lupis familiaris

<400> SEQUENCE: 14
tccgatccga tacttcaagt aagtggtgtt tggtcgccgc agattaaa              48

<210> SEQ ID NO 15
<211> LENGTH: 48
<212> TYPE: DNA
<213> ORGANISM: Canis lupis familiaris

<400> SEQUENCE: 15
tccgatccgt cgcttcaagt aagtggtgtt tggtcgccgc cgaccaag              48

<210> SEQ ID NO 16
<211> LENGTH: 48
<212> TYPE: DNA
<213> ORGANISM: Canis lupis familiaris

<400> SEQUENCE: 16
tccgatccgt cgcttcaagt aagtggtgtt tggtcgccgc agaccaag              48

<210> SEQ ID NO 17
<211> LENGTH: 48
<212> TYPE: DNA
<213> ORGANISM: Canis lupis familiaris

<400> SEQUENCE: 17
tccgatccgt cgcttcaagt aagtggtgtt tggtcgccgc agattaaa              48

<210> SEQ ID NO 18
<211> LENGTH: 48
<212> TYPE: DNA
<213> ORGANISM: Canis lupis familiaris

<400> SEQUENCE: 18
tccgatccgt cgcttcaagt aagtggtgtt tggtcgccgc agatcaga              48
```

```
<210> SEQ ID NO 19
<211> LENGTH: 48
<212> TYPE: DNA
<213> ORGANISM: Canis lupis familiaris

<400> SEQUENCE: 19
tccgatccgt tacttcaagt aagtggtgtt tggtcgccgc agattaaa          48

<210> SEQ ID NO 20
<211> LENGTH: 48
<212> TYPE: DNA
<213> ORGANISM: Canis lupis familiaris

<400> SEQUENCE: 20
ccccacaggt tatcccaagt aagtggtgtt tggtcgccgc agattaaa          48

<210> SEQ ID NO 21
<211> LENGTH: 48
<212> TYPE: DNA
<213> ORGANISM: Canis lupis familiaris

<400> SEQUENCE: 21
ccccacagta tacttcaagt aagtggtgtt tggtcgccgc cgaccaag          48

<210> SEQ ID NO 22
<211> LENGTH: 48
<212> TYPE: DNA
<213> ORGANISM: Canis lupis familiaris

<400> SEQUENCE: 22
ccccacagta tacttcaagt aagtggtgtt tggtcgccgc agattaag          48

<210> SEQ ID NO 23
<211> LENGTH: 48
<212> TYPE: DNA
<213> ORGANISM: Canis lupis familiaris

<400> SEQUENCE: 23
ccccacagta tacttcaagt aagtggtgtt tggtcgccgc agattaaa          48

<210> SEQ ID NO 24
<211> LENGTH: 48
<212> TYPE: DNA
<213> ORGANISM: Canis lupis familiaris

<400> SEQUENCE: 24
ccccacagta tatccccggc aagtggtgcc cgatcgcccc cgattcaa          48

<210> SEQ ID NO 25
<211> LENGTH: 48
<212> TYPE: DNA
<213> ORGANISM: Canis lupis familiaris

<400> SEQUENCE: 25
cccgatccgt cgcttcaagt aagtggtgtt tggtcgccgc agattaaa          48

<210> SEQ ID NO 26
<211> LENGTH: 48
<212> TYPE: DNA
<213> ORGANISM: Canis lupis familiaris

<400> SEQUENCE: 26
cctcacagta tatccccggc aagtggtgcc cgatcgcccc cgattcaa          48
```

-continued

```
<210> SEQ ID NO 27
<211> LENGTH: 48
<212> TYPE: DNA
<213> ORGANISM: Canis lupis familiaris

<400> SEQUENCE: 27
ctccacagta tatccccggc aagtggtgcc cgatcgcccc cgattcaa          48

<210> SEQ ID NO 28
<211> LENGTH: 48
<212> TYPE: DNA
<213> ORGANISM: Canis lupis familiaris

<400> SEQUENCE: 28
ctccgtaggt cgcttcaagt aagtggtgtt tggtcgccgc agattaaa          48

<210> SEQ ID NO 29
<211> LENGTH: 48
<212> TYPE: DNA
<213> ORGANISM: Canis lupis familiaris

<400> SEQUENCE: 29
ctcgaccgta tacttcaagt aagtggtgtt tggtcgccgc agattaag          48

<210> SEQ ID NO 30
<211> LENGTH: 48
<212> TYPE: DNA
<213> ORGANISM: Canis lupis familiaris

<400> SEQUENCE: 30
ctcgaccgtt cgcttcaagt aagtggtgtt tggtcgccgc agatcaga          48

<210> SEQ ID NO 31
<211> LENGTH: 48
<212> TYPE: DNA
<213> ORGANISM: Canis lupis familiaris

<400> SEQUENCE: 31
ctcgacccgt cgcttcaagt aagtggtgtt tggtcgccgc cgaccaag          48

<210> SEQ ID NO 32
<211> LENGTH: 48
<212> TYPE: DNA
<213> ORGANISM: Canis lupis familiaris

<400> SEQUENCE: 32
ctcgacccgt cgcttcaagt aagtggtgtt tggtcgccgc agattaaa          48

<210> SEQ ID NO 33
<211> LENGTH: 48
<212> TYPE: DNA
<213> ORGANISM: Canis lupis familiaris

<400> SEQUENCE: 33
ctcgatccgt cgcttcaagt aagtggtgtt tggtcgccgc caacccaa          48

<210> SEQ ID NO 34
<211> LENGTH: 48
<212> TYPE: DNA
<213> ORGANISM: Canis lupis familiaris

<400> SEQUENCE: 34
ctcgatccgt cgcttcaagt aagtggtgtt tggtcgccgc agattaaa          48
```

```
<210> SEQ ID NO 35
<211> LENGTH: 48
<212> TYPE: DNA
<213> ORGANISM: Canis lupis familiaris

<400> SEQUENCE: 35
cttcgccggt cgcttcaagt aagtggtgtt tggtcgccgc agactaga         48

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
caatccccat aatgccacag                                        20

<210> SEQ ID NO 37
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
acgacgtctg cggacaag                                          18

<210> SEQ ID NO 38
<211> LENGTH: 429
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38
gggggccgcg cgcaggcact cggagcgcgc ggctgcagca gaggagccgg agccgggaac    60
cggagccggg agccggagcc gcggccggat cgcagcccgc ggggcccgcc gcagccatgg   120
gcaaccgcgg catggaggat ctcatcccgc tagtcaaccg gctgcaggac gccttctccg   180
ctatcggcca gaacgcggac ctcgacctac cgcagatcgc ggtggtgggc ggccagagcg   240
ccggcaagag ctcggtgctc gagaatttcg taggcaggta ggagcggcgc gccccggagc   300
gcgaactgcc cccgcccggg tccccggggcc tccgccccca gccccgacgg cgccgcgacc   360
tcgcagccct tggcgctgcc cccgcggacc gcgcgccccc ctcctccagc cagacggagg   420
gcgccccccc                                                   429

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
ttctcagctg ccatctctcc                                        20
```

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
gaagagtggg ggagggtaag                                              20

<210> SEQ ID NO 41
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
taaggtgtgg tgggcacttt gggagagagt tggarctccc agtgrcagga tgtgtgcccc    60
caggacacag ggagcccatt caggccttga ctcattgcta ctctcactcc caactcattg   120
cagggacttc ctgccccgag ggtcaggcat tgtcacccga cggcccctgg tcctgcagct   180
ggtcaatgcc accacaggta tgcgctctct ggaccagcac tcgacccggc ctctccagcg   240
tccccacctt atccccaagg agaggtctgg cctagccgct gaacttgctt gcttctagga   300
ctttggcact gattcccctt ctggacagtg gggataaaat gcataacgaa gacatggcgt   360
tgttgtgggg agggagtg                                                 378

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
aaggagaggt ctggcctagc                                              20

<210> SEQ ID NO 43
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43 ctggggcgg atctaagac                                                19

<210> SEQ ID NO 44
<211> LENGTH: 451
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
aggagaggtc tggcctagcc gctgaacttg cttgcttcta ggactttggc actgattccc      60
cttctggaca gtggggataa aatgcataac gaagacatgg cgttgttgtg gggagggagt     120
ggggagaagg cagtgtttcg gggtgtgtgt gggtctattt ccaggggaag atgggaccta     180
ggtgggttgg ggttagaatg cttaccctcc cccactcttc cccacgtccc cttctgggac     240
agaatatgcc gaattcctgc actgcaaggg gaagaaattc actgacttcg aggaggtacg     300
cctggagatc gaggctgaga ccgaccgggt cactggcacc aacaagggca tctcgccggt     360
gcccatcaac ctccgcgtct actcgcctca gggtgaggag tcgtgtcccc gccccaggcc     420
ttcgggctcc cggtcttaga tccgccccca g                                    451
```

<210> SEQ ID NO 45
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45

```
ccctctcgcc accctgtc                                                    18
```

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46

```
ctgcccttag gaacctaccc                                                  20
```

<210> SEQ ID NO 47
<211> LENGTH: 242
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

```
ccctctcgcc acctgtccag tcctgaatct gacactggtg gacctacccg gaatgaccaa      60
ggtcccagtg ggggaccaac ctcctgacat cgagttccag atccgggaca tgcttatgca     120
gttcgtcacc aaagagaact gcctcatcct ggctgtgtcc cccgccaact ccgacctggc     180
caactctgat gctctcaagg ttgccaagga ggtggacccc cagggtaggt tcctaagggc     240
ag                                                                    242
```

<210> SEQ ID NO 48
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 48

```
atgggcaacc gcggcatgga ggatctcatc ccgctagtca accggctgca ggacgccttc      60
```

```
tccgctatcg gccagaacgc ggacctcgac ctaccgcaga tcgcggtggt gggcggccag    120
agcgccggca agagctcggt gctcgagaat tcgtaggca g                         161
```

<210> SEQ ID NO 49
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49

```
ggacttcctg ccccgagggt caggcattgt cacccgacgg ccctggtcc tgcagctggt    60 caatgccacc acag                                                       74
```

<210> SEQ ID NO 50
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

```
aatatgccga attcctgcac tgcaagggga agaaattcac tgacttcgag gaggtacgcc    60
tggagatcga ggctgagacc gaccgggtca ctggcaccaa caagggcatc tcgccggtgc   120
ccatcaacct ccgcgtctac tcgcctcagg                                     150
```

<210> SEQ ID NO 51
<211> LENGTH: 204
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51

```
tcctgaatct gacactggtg gacctacccg gaatgaccaa ggtcccagtg ggggaccaac    60
ctcctgacat cgagttccag atccgggaca tgcttatgca gttcgtcacc aaagagaact   120
gcctcatcct ggctgtgtcc cccgccaact ccgacctggc caactctgat gctctcaagg   180
ttgccaagga ggtggacccc cagg                                           204
```

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52

```
aatgaggctg gagagcagag                                                 20
```

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 53
tgaggacact aaccccctgtt g                                      21

<210> SEQ ID NO 54
<211> LENGTH: 520
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
gagagcagag gcaggtagtg ggtgagggag ggtgtgggta gggagatgtg ggaagcaggt    60
ggagtgcatg tggtctccct tgtgaggaga gcatgtgcag atgtaggtga ccctctcctg   120
ctgtccccta ggtcagcgca ccatyggggt catcaccaag ctagatctga tggaygaggg   180
cacagatgcc cgagatgtgc tagagaataa gctccttccc ctgcgcagag gtaggtaggc   240
tctccgaccc actccacctg cccttcttca ccccaccctg tgcgaggctg gttgccctg    300 acttcggccc ccttccacag gctacatagg ggtggtaaac cgaagccaga aggacattga   360
tggcaagaag gacatctcag ctgccttggc ygctgaackc aagttctttc tctcccaccc   420
atcctaccgc cacttggcgg accgcatggg cacaccctac ctacagaagg tcctcaacca   480
ggtaaggaac tcaggcctgg ggaaagcagc gyggggacag                         520

<210> SEQ ID NO 55
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ctgtgggcat ctccatttg                                          19

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
gcggctcact ttatcactcc                                         20

<210> SEQ ID NO 57
<211> LENGTH: 718
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
tccgcctccc ctcccccctc agcaactgac caaccacatc cgggacacac tgccggggct    60
ccggaacagg ctgcagagcc agctactgtc cattgagaag gaggtggagg agtacaagaa   120

```
cttccgacct gatgacccag cacgcaagac caaggccctg ctgcagtgag gcccgcccca    180
actcctgaca ccccagcact gagctgcccc tctgcaccgg gctctctcag ggctctctcc    240
acccagggct ccctgcacaa ggctgctgca gcccccctcac gccatcccac tctctccatc   300
ccccaggatg gtccagcagt ttgctgtgga ctttgagaag cgcattgagg gctccgggga    360
ccagattgac acctatgaac tgtcaggggg agcccgcatc aaccggatct ccatgagcg     420 cttcccttt gagctagtca aggtaggaca gtctccccag gggcagagtg ggggagctta    480
ggactaccca ccctscccctc caggacttcc acatgaacct ttgctgacct ggtgccgata   540
gggagtgggg cctctgtctt ggccttctag ggagcaggaa ggcctgacca gctgcctctt    600
gctctcctgc acagatggag tttgatgaga aggagctccg gagagagatc agctacgcca    660
tcaagaacat ccatggcatt aggcacgtat tgggaccggg gaaaggggct gagccctg      718
```

```
<210> SEQ ID NO 58
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
```

```
gtcagcgcac catyggggtc atcaccaagc tagatctgat ggaygagggc acagatgccc    60
gagatgtgct agagaataag ctccttcccc tgcgcagag                           99
```

```
<210> SEQ ID NO 59
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
```

```
gctacatagg ggtggtaaac cgaagccaga aggacattga tggcaagaag gacatctcag    60
ctgccttggc ygctgaacgc aagttctttc tctcccaccc atcctaccgc cacttggcgg    120
accgcatggg cacaccctac ctacagaagg tcctcaacca g                       161
```

```
<210> SEQ ID NO 60
<211> LENGTH: 143
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60
```

```
caactgacca accacatccg ggacacactg ccggggctcc ggaacaggct gcagagccag    60
ctactgtcca ttgagaagga ggtggaggag tacaagaact ccgacctga tgacccagca     120 cgcaagacca aggccctgct gca                                            143
```

```
<210> SEQ ID NO 61
<211> LENGTH: 136
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 61
gatggtccag cagtttgctg tggactttga gaagcgcatt gagggctccg gggaccagat    60
tgacacctat gaactgtcag ggggagcccg catcaaccgg atcttccatg agcgcttccc   120
ctttgagcta gtcaag                                                  136

<210> SEQ ID NO 62
<211> LENGTH: 68
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
atggagtttg atgagaagga gctccggaga gagatcagct acgccatcaa gaacatccat    60
ggcattag                                                            68

<210> SEQ ID NO 63
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ataagcagac cttgccttgc                                                20

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
cttcagagag gccccttgtc                                                20

<210> SEQ ID NO 65
<211> LENGTH: 479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
gtcctccatt agaatccctc ccgcccattt tacagatgag gacactgaag cccagagagg    60
ggtaatagcg ggaggacccc aaggagaaat caggggtcg ggtgggccct ggcctagcac    120
tcctggtagg agctggcctg tgacactgtg cccttctccc gctccgggcg ttcagaacgg   180
ggctctttac cccagacatg gcttttgaga ccattgtgaa aaagcaggtg aagaagatcc   240
gagaaccgtg tctcaagtgt gtggacatgg ttatctcgga actaatcagc acggttagac   300
agtgcaccaa gaaggtaacc cggtggcccr ggcagccccc cccacctctg tccccatcct   360
gcactgctgc caggcgctct ttccccacac ccccactgc ctcctcggta gcatgtacag    420

```
acctcagcgg ggtgggggag gcaggccacc ccagacccag acaagggggcc tctctgaag    479
```

<210> SEQ ID NO 66
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66

```
accctcgagt tgtcatttgg                                                 20
```

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67

```
gggtatgaca gatggggatg                                                 20
```

<210> SEQ ID NO 68
<211> LENGTH: 492
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

```
ggcttggtgc cttcagcttc ctggggaccc caggcctctc ttcccctcat cccgggcctt    60
ctgtgtgtgc ctcccacgcc acgcccctgg atccccggat tctggtgggg tggaggagct   120
ccccgccagt gccccctgtg tacgtggctc tctcccctcc cgcccctccc cagctgcagc   180
agtaccccccg gctgcgggag gagatggagc gcatcgtgac cacccacatc cgggagcgtg   240
agggtcgcac caaggagcag gtgagtccac agcccctcct gccccctgggc cctcctccct   300
ctccttccca ttttgcctct tctgtctytg tctccctcac gctttctggc ctcacactct   360
ctgcttctct ctcttttttt tactggggga aaaatttttc caactaaaaa ataccccctt   420
ggccacctct caatgaacgg gtcaatggta ttaaacacat ttccccctggt ggggccccct   480
catccccatc cg                                                        492
```

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69

```
tttcttccag cctttcatgc                                                 20
```

<210> SEQ ID NO 70
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 70
cagctcaagc caaagagtgc                                                 20

<210> SEQ ID NO 71
<211> LENGTH: 420
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
acctgcatat yctcaaaggt tatgctcctc atcgatattg agctggcgta catgaatacc     60
aatcatgagg acttcatagg ctttgccaag tgagtgctcc ctaggctaag aagtgacacc    120
tctagtgtgt gtgtgtgtgt gtgtgtagga cccaggcctg ttgggttaac cctctgggtc    180
tggtgcccac tgagcagtgg cattgaagct aggcctcttg agaggagaag ttctgagact    240
cttccttctc ttcttcttag tgctcagcag aggagcaacc agatgaacaa gaagaaggct    300
tcagggaacc aggtgagtga accccagtgc cccagccgga gggatggagg gtgccggatg    360
gacgccaagc tctgagagcc ccctcccccg aggggaaggg tctcacaggg gccagggatc    420

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
ttaaccctct gggtctggtg                                                 20

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
ctggtatgtg caagcagctc                                                 20

<210> SEQ ID NO 74
<211> LENGTH: 440
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
tttaaccctc tgggtctggt gcccactgag cagtggcatt gaagctaggc ctcttgagag     60
gagaagttct gagactcttc cttctcttct tcttagtgct cagcagagga gcaaccagat    120
gaacaagaag aaggcttcag ggaaccaggt gagtgaaccc cagtgcccca gccggaggga    180
```

```
tggagggtgc cggatggacg ccaagctctg agagccccct cccccgaggg gaagggtctc    240
acagggccca gggatcctat cagctgccag ccacaagcct cccactctgc ctcagtaacc    300
ctctctcctc tctcccgatg cttctcgtgg ttgctatggt tacctctttg caggatgaga    360
ttctggtgag taccaggact ggggctcttg gcttgtatag cgaaggggag gaggggaccc    420
attagtagtg gggatgccca                                                440
```

```
<210> SEQ ID NO 75
<211> LENGTH: 139
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
```

```
aacggggctc tttaccccag acatggcttt tgagaccatt gtgaaaaagc aggtgaagaa     60
gatccgagaa ccgtgtctca agtgtgtgga catggttatc tcggaactaa tcagcacggt    120
tagacagtgc accaagaag                                                 139
```

```
<210> SEQ ID NO 76
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
```

```
ctgcagcagt accccggct gcgggaggag atggagcgca tcgtgaccac ccacatccgg     60
gagcgtgagg gtcgcaccaa ggagcag                                        87
```

```
<210> SEQ ID NO 77
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
```

```
gttatgctcc tcatcgatat tgagctggcg tacatgaata ccaatcatga ggacttcata     60
ggctttgcca a                                                         71
```

```
<210> SEQ ID NO 78
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
```

```
tgctcagcag aggagcaacc agatgaacaa gaagaaggct tcagggaacc ag             52
```

```
<210> SEQ ID NO 79
<211> LENGTH: 12
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 79
gatgagattc tg                                                         12

<210> SEQ ID NO 80
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
tgagctgacc tatgccttcc                                                 20

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
ttctctttcc cacctggatg                                                 20

<210> SEQ ID NO 82
<211> LENGTH: 389
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
acagggcagg tctggcccac accctccctg cccagccagg cttccaagag ctggaggagg     60
ggtgggcttt tgagtgtttc tctttgccta ccccatcctc cagggagagt cctggcctct    120
ccccactgac ctcctgccct ctcacccctcc aggtcatccg gaagggctgg ctgaccatca   180
acaatattgg catcatgaag gggggctcca aggagtactg gtttgtcctg accgctgaga    240
atctgtcctg gtacaaggat gacgaggtga gtaaagggcc actggtcatc aaagggtttg    300
gctggggcca gattcaggct cagacactac tccaagggct tggagtagat tgggccaccc    360
aacaaacaaa gtttttttt ttttttttt                                       389

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
actgggaacc agaggtgctc                                                 20

<210> SEQ ID NO 84
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
gcagggtgtc ttaggcagag                                                   20

<210> SEQ ID NO 85
<211> LENGTH: 402
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85 gcaggggggca tgggtgccca gaaacccagg gcygccctgg ggctccagag ccctgctccc      60
ccactgcccc aaacctccgc atggaacact cttaggatat gaggcatggc accgacctca     120
cccatcgctc ccacctctat ccacaggaga aagagaagaa atacatgctc tccgtggaca     180
atctgaagct acgggacgtg gagaaaggtt tcatgtcaag caagcacatc tttgccctct     240
ttaacactga gcagaggtgg gtccccagac tgcaagcccc aaaccacctt tcctgagcag     300
aaaggagagg gacctgctcc aagccccaca gcgagagtca ttcctttgac aaatattcag     360
tcaatcactt ggtaagcgcc tgctctgcct aagacaccct gc                        402

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
cttccaggca aggaaacaag                                                   20

<210> SEQ ID NO 87
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
aggaattgcc atctgtggtc                                                   20

<210> SEQ ID NO 88
<211> LENGTH: 440
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
cttccaggca aggaaacaag cttgggaggt gagggacat gcccagggtc acacagctgg       60
gaaatgagga agccaggact gggccccagg tgtgatgtcc ccagtctgtg catgccctta    120
```

```
atcacctggg tgagtgggtc tccgagcctt ctccctcgc cgcctgcccc accttgcagg      180
aatgtctaca aggattatcg gcagctggaa ctggcctgtg agacrcaaga ggaggtggat      240
agctggaagg cctctttcct gcgggctggc gtatatcctg aacgcgttgg ggtgagtgga      300
agggcaggga gggggcaag ttacttctaa taggggccc tgaatcacta tcctcagcga       360
tgccaagtca tgtcatcagg gctcagaaat agcacagatc ctccccctta cctgtactgg      420
ggtgggatca gagttaagcc                                                 440
```

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89

```
gtgtgtctgc tttggctgtg                                                  20
```

<210> SEQ ID NO 90
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90

```
ccacccctt cctgattc                                                     18
```

<210> SEQ ID NO 91
<211> LENGTH: 149
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

```
ggtgtgtctg ctttggctgt gcttgctggt ggcggcggcg gtggtggtgg caatgctggt      60
gtcrtggcct ctatggcttt ggtgtgggcc tcccaggaca aggagaaagt gagtgtgccc      120
ctctctcacc ttctkccagg tgtctccag                                       149
```

<210> SEQ ID NO 92
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92

```
agttctccag gcacccttc                                                   19
```

<210> SEQ ID NO 93
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 93
atcccaaggg actggtctg                                                19

<210> SEQ ID NO 94
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
agttctccag gcaccyttca aggggctgag accctgggag tggctggaac ctggctacga     60
gggcccagyc rctctgatgc cctctattct caacggcagg ccagcgaaac agaggagaat    120
ggctcagaca gcttcatgca ctccatggac ccacagctag agcggcaggt ggagaccatc    180
cggaacctgg tagactcata catggccatc gtgaacaaga ccgtgcgtga cctcatgccg    240
aagaccatca tgcacctcat gatcaacaat gtgggtgcaa cacttygtgg gcagtgggtg    300
ctcttttggg accagggagg ga                                             322

<210> SEQ ID NO 95
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95 ttttttttt                                                             9

<210> SEQ ID NO 96
<211> LENGTH: 114
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
gtcatccgga agggctggct gaccatcaac aatattggca tcatgaaggg gggctccaag     60
gagtactggt ttgtcctgac cgctgagaat ctgtcctggt acaaggatga cgag          114

<210> SEQ ID NO 97
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gagaaagaga agaaatacat gctctccgtg gacaatctga agctacggga cgtggagaaa     60
ggtttcatgt caagcaagca catctttgcc ctctttaaca ctgagcagag                110

<210> SEQ ID NO 98
<211> LENGTH: 112
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
gaatgtctac aaggattatc ggcagctgga actggcctgt gagacgcaag aggaggtgga    60
tagctggaag gcctctttcc tgcgggctgg cgtatatcct gaacgcgttg gg           112

<210> SEQ ID NO 99
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gacaaggaga aa                                                        12

<210> SEQ ID NO 100
<211> LENGTH: 171
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
gccagcgaaa cagaggagaa tggctcagac agcttcatgc actccatgga cccacagcta    60
gagcggcagg tggagaccat ccggaacctg gtagactcat acatggccat cgtgaacaag   120
accgtgcgtg acctcatgcc gaagaccatc atgcacctca tgatcaacaa t            171

<210> SEQ ID NO 101
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
aaagggcaag catggagac                                                 19

<210> SEQ ID NO 102
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
tccgaagttc cagctccac                                                 19

<210> SEQ ID NO 103
<211> LENGTH: 515
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 103

```
catggagacg ggaaagcggg ggagatctct gagtggcaaa gccaggacca ccgagctccc      60
agtccagcgc acggtccccc aaggcggcca gactggcaca ggcgtcaggt cctagcccct     120
cctctcttgg cgcgcccgca gacgaaggaa ttcatcttct cggagctgct cgccaacctg     180
tactcgtgcg ggaccagaa cacactgatg gaggagtcgg cggagcaggc gcaacggcgc      240
gacgagatgc tgcgcatgta ccacgcactg aaggaggcgc tcagcatcat cggcgatatc     300
aacacgacca ccgtcagcac gcccatgccc ccgcccgtgg acgactcctg gctgcaggtg     360
cagagcgtac cggccggacg caggtaccag ggccggcccc acggccccca agcccccca      420
acccggggcc cgcggggaggt gggccgggac cgggcagtgg cgcgcccgcg tcaccggaac    480
ggctcccacc tggagcaggg ggcggggctt agaga                                515
```

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 104

```
taacctccgg gaacgagtag                                                  20
```

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 105

```
tagaaagaag ggggcaggtg                                                  20
```

<210> SEQ ID NO 106
<211> LENGTH: 189
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

```
ctggggcggg gcctcaggat ggggcggagc tactcatctc ctccctcctt gttttccgcg      60
ccctgtcgtc cgcaggtcac ccacgtccag ccccacgccg cagcgccgag ccccgccgt      120
gccccagcc cggcccgggt cgcggggccc tgctcctggg cctccgcctg ctgggtccgc      180
cctgggggg                                                             189
```

<210> SEQ ID NO 107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 107
ctcctccctc cttgttttcc                                            20

<210> SEQ ID NO 108
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
gtcctagcgc cctggatg                                              18

<210> SEQ ID NO 109
<211> LENGTH: 263
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
ggtcacccac gtccagcccc acgccgcagc gccgagcccc cgccgtgccc ccagcccggc   60
ccgggtcgcg gggccctgct cctgggcctc cgcctgctgg gtccgccctg ggggggggcgc  120 ccccccgtgcc ctccaggccg ggggcttccc ctgaccccctt cggtcctccc ccccaggtgc 180
cctcgcgccc caaccgcgcc ccgcccgggg tccccaggtg agtaggggct gaatgcggcg  240
ggagagacca ccgggcgggc gta                                         263

<210> SEQ ID NO 110
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
gcccttgcct taccagttc                                             19

<210> SEQ ID NO 111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
gggagccact gtcaagtcac                                            20

<210> SEQ ID NO 112
<211> LENGTH: 205
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
```

```
gcccttgcct taccagttct cttcctcctt ctctccgttc tcttttttgct ttctctccac    60 tgccagccga tcgggtcagg caagtccgtc ccgtcctgag agccccaggc ccccttcga    120 cctctaacca gatccctcta ttcctcggag acctccctttt ccaagcctgc ctggacggct   180
gttctgtgac ttgacagtgg ctccc                                          205
```

<210> SEQ ID NO 113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113

```
gtaggctctc cgacccactc                                                 20
```

<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114

```
tgaggacact aacccctgtt g                                               21
```

<210> SEQ ID NO 115
<211> LENGTH: 511
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115

```
tagggagatg tgggaagcag gtggagtgca tgtggtctcc cttgtgagga gagcatgtgc     60
agatgtaggt gaccctctcc tgctgtcccc taggtcagcg caccatcggg gtcatcacca   120
agctagatct gatggatgag ggcacagatg cccgagatgt gctagagaat aagctccttc   180
ccctgcgcag aggtaggtag gctctccgac ccactccacc tgcccttctt caccccaccc   240
tgtgcgaggc tggttgcccc tgacttcggc cccctttccac aggctacata ggggtggtaa   300
accgaagcca gaaggacatt gatggcaaga aggacatctc agctgccttg gcygctgaac   360
gcaagttctt tctctcccac ccatcctacc gccacttggc ggaccgcatg ggcacaccct   420
acctacagaa ggtcctcaac caggtaagga actcaggcct ggggaaagca gcgtgggggac   480 aggtatattt aaatgtgttt tgtgaaggtg a                                   511
```

<210> SEQ ID NO 116
<211> LENGTH: 242
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116

```
acgaaggaat tcatcttctc ggagctgctc gccaacctgt actcgtgcgg ggaccagaac     60
```

```
acactgatgg aggagtcggc ggagcaggcg caacggcgcg acgagatgct gcgcatgtac    120
cacgcactga aggaggcgct cagcatcatc ggcgatatca acacgaccac cgtcagcacg    180
cccatgcccc cgcccgtgga cgactcctgg ctgcaggtgc agagcgtacc ggccggacgc    240
ag                                                                   242
```

<210> SEQ ID NO 117
<211> LENGTH: 220
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117

```
gtcacccacg tccagcccca cgccgcagcg ccgagccccc gccgtgcccc cagcccggcc     60
cgggtcgcgg ggccctgctc ctgggcctcc gcctgctggg tccgccctgg ggggggcgcc    120
ccccgtgccc tccaggccgg gggcttcccc tgaccccttc ggtcctcccc cccaggtgcc    180
ctcgcgcccc aaccgcgccc cgcccggggt ccccaggtga                          220
```

<210> SEQ ID NO 118
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118

```
ccgatcgggt caggcaagtc cgtcccgtcc tgagagcccc aggccccct tcgacctcta      60 a                                                                     61
```

<210> SEQ ID NO 119
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119

```
gctacatagg ggtggtaaac cgaagccaga aggacattga tggcaagaag gacatctcag     60
ctgccttggc ygctgaacgc aagttctttc tctcccaccc atcctaccgc cacttggcgg    120
accgcatggg cacaccctac ctacagaagg tcctcaacca g                        161
```

<210> SEQ ID NO 120
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120

```
agcctgtgcg aagtctgg                                                   18
```

<210> SEQ ID NO 121
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
cagatcaccc agtgaaggag                                                  20

<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
gtaggctctc cgacccactc                                                  20

<210> SEQ ID NO 123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
tgaggacact aacccctgtt g                                                21

<210> SEQ ID NO 124
<211> LENGTH: 30
<212> TYPE: PRT
<213> ORGANISM: Mus musculus

<400> SEQUENCE: 124

Asp Ile Glu Gly Lys Lys Asp Ile Arg Ala Ala Leu Ala Ala Glu Arg
1               5                   10                  15
Lys Phe Phe Leu Ser His Pro Ala Tyr Arg His Met Ala Asp
            20                  25                  30

<210> SEQ ID NO 125
<211> LENGTH: 30
<212> TYPE: PRT
<213> ORGANISM: Mus musculus

<400> SEQUENCE: 125

Asp Ile Asp Gly Lys Lys Asp Ile Lys Ala Ala Met Leu Ala Glu Arg
1               5                   10                  15
Lys Phe Phe Leu Ser His Pro Ala Tyr Arg His Ile Ala Asp
            20                  25                  30

<210> SEQ ID NO 126
<211> LENGTH: 30
<212> TYPE: PRT
<213> ORGANISM: Mus musculus

<400> SEQUENCE: 126

Asp Ile Asp Gly Lys Lys Asp Ile Thr Ala Ala Leu Ala Ala Glu Arg
1               5                   10                  15
Lys Phe Phe Leu Ser His Pro Ser Tyr Arg His Leu Ala Asp
            20                  25                  30
```

```
<210> SEQ ID NO 127
<211> LENGTH: 30
<212> TYPE: PRT
<213> ORGANISM: Bos taurus

<400> SEQUENCE: 127

Asp Ile Asp Gly Lys Lys Asp Ile Thr Ala Ala Leu Ala Ala Glu Arg
1               5                   10                  15

Lys Phe Phe Leu Ser His Pro Ser Tyr Arg His Leu Ala Asp
            20                  25                  30

<210> SEQ ID NO 128
<211> LENGTH: 48
<212> TYPE: DNA
<213> ORGANISM: Canis lupis familiaris

<400> SEQUENCE: 128
tccgatccgt cgcttcaagt aagtggtgtt tggtcgccgc agattaaa              48
```

METHOD OF DETECTING CANINE EXERCISE-INDUCED COLLAPSE

RELATED APPLICATIONS

This application claims priority to U.S. Provisional Application No. 61/123,753 that was filed on Apr. 9, 2008.

BACKGROUND OF THE INVENTION

Diseases of the nervous system are responsible for a significant proportion of human health problems. Genetic mutations for several major forms of neurological disease, including epilepsies and neuropathies, have been documented. Due to the human-animal bond, companion animals have health surveillance second only to people, making companion animals and dogs in particular ideal models for many health conditions. Canine models have helped to define the molecular basis and treatment of a number of neurological diseases including narcolepsy, Lafora disease, and lysosomal storage diseases. While the physiology of neurotransmitters and their respective receptors has been extensively detailed for decades, the biology of neurotransmitter synaptic vesicles and associated proteins is just starting to be elucidated. Dynamin 1 (DNM1) is critically important for synaptic vesicle recycling during high level neurological stimulation.

Labrador Retrievers are the most common dog breed in the world, with over 123,760 new US registrations in 2006 alone. Over the last 100 years, with the advent of kennel clubs, dog shows, and very specific dog breed standards, inbreeding within dog breeds has increased dramatically. More than 370 Mendelian diseases have been documented in dogs, with over 70% of them autosomal recessive and 46% breed specific. The high breed specificity is most likely due to deleterious recessive mutations being propagated and concentrated by the founder effect or popular sires being bred repeatedly.

Exercise Induced Collapse (EIC) is a newly characterized syndrome of dogs. The condition has been best described in Labrador Retrievers, but dogs from a number of other breeds are known to have a similar condition. Dogs considered to suffer from EIC usually start to develop signs of an episode 5-15 minutes after the initiation of strenuous "high-excitement" exercise such as retrieving training dummies or birds. At the beginning of the EIC episode the dog starts to lose coordination and develops a 'wobbly' gait, which soon progresses to a loss of control of their hind legs. Sometimes the episode affects the entire body, during which the dog is unable to move. The collapse episode usually lasts for 5-10 minutes, and after 30 minutes the dog will have almost completely recovered. EIC affected dogs typically appear to be in excellent physical condition, and usually have very good muscle tone, which is different from many other causes of exercise intolerance.

SUMMARY OF THE INVENTION

The present invention features assays for determining whether a dog has or is susceptible to developing Exercise Induced Collapse (EIC). In one embodiment, the method comprises determining whether an allele associated with the disease is present in a nucleic acid from the subject. In certain embodiments the allele is dynamin 1 (G767T) or an allele in linkage disequilibrium with the dynamin 1 (G767T) allele. The detection of the dynamin 1 (G767T) allele or an allele in linkage disequilibrium with the dynamin 1 (G767T) allele is indicative that the dog has or is predisposed to the development of EIC.

Appropriate alleles can be detected by any of a variety of means, including: 1) performing a hybridization reaction between the nucleic acid sample and a probe or probes that are capable of hybridizing to the allele; 2) sequencing at least a portion of the allele; or 3) determining the electrophoretic mobility of the allele or a component thereof. In one embodiment, the allele is subject to an amplification step, prior to or in conjunction with the performance of the detection step. In certain embodiments, amplification steps are by polymerase chain reaction (PCR), ligase chain reaction (LCR), strand displacement amplification (SDA), cloning, and variations of the above (e.g., RT-PCR and allele specific amplification). In one embodiment, the sample is hybridized with a set of primers, which hybridize 5' and 3' to a sense or antisense sequence of an allele and is subject to a PCR amplification.

In one embodiment, the detecting step is by allele specific hybridization followed by primer specific extension. In one embodiment, prior to or in conjunction with detection, the nucleic acid sample is subject to an amplification step. In one embodiment, the size analysis is preceded by a restriction enzyme digestion. In one embodiment, dynamin 1 or a portion thereof is amplified. In one embodiment, at least one oligonucleotide probe is immobilized on a solid surface.

In another aspect, the invention features kits for performing the above-described assays. The kit can include DNA sample collection means and a means for determining an allele that is indicative of EIC in a dog. In one embodiment, the kit contains a first primer oligonucleotide that hybridizes 5' or 3' to an allele selected from the group consisting of a dynamin 1 (G767T) allele and alleles in linkage disequilibrium with the dynamin 1 (G767T) allele. In one embodiment, the kit additionally comprises a second primer oligonucleotide that hybridizes either 3' or 5' respectively to the allele, so that the allele can be amplified. In one embodiment, first primer and the second primer hybridize to a region in the range of between about 50 and about 1000 base pairs. In one embodiment, the kit additionally comprises a detection means. In certain embodiments, the detection means is by a) allele specific hybridization; b) size analysis; c) sequencing; d) hybridization; e) 5' nuclease digestion; f) single-stranded conformation polymorphism; g) primer specific extension; and/or h) oligonucleotide ligation assay. In certain embodiments, the kit additionally comprises an amplification means.

Information obtained using the assays and kits described herein is useful for determining whether a dog has or is susceptible to developing EIC. In addition, the information allows customization of therapy to the dog's genetic profile.

The present invention provides a method for detecting the presence of a biomarker associated with canine Exercise Induced Collapse (EIC). In one embodiment of the invention, the method involves obtaining a physiological sample from a dog, wherein the sample comprises nucleic acid, and determining the presence of the biomarker. As used herein, the phrase "physiological sample" is meant to refer to a biological sample obtained from a mammal that contains nucleic acid. For example, a physiological sample can be a sample collected from an individual dog, such as including, but not limited to, e.g., a cell sample, such as a blood cell, e.g., a lymphocyte, a peripheral blood cell; a tissue sample such as mucosal sample (e.g., cheek swab) or muscle tissue, e.g., skeletal muscle; an organ sample, e.g., liver or skin; a hair sample, e.g., a hair sample with roots; and/or a fluid sample, such as blood.

Examples of breeds of affected dogs include, but are not limited to, Labrador Retrievers, Chesapeake Bay Retrievers, Curly-Coated Retrievers, Border Collies, or other related or unrelated breeds. The method of the present invention also includes dogs of crossed or mixed breeds.

The present invention further provides a method for determining whether a dog has or is predisposed to developing an Exercise Induced Collapse (EIC), which involves (a) transporting a biological sample from a dog suspected of having or being predisposed to developing EIC to a diagnostic laboratory, (b) detecting in a nucleic acid sample from the dog, an EIC associated allele, which is selected from the group consisting of a dynamin 1 (G767T) allele and any allele in linkage disequilibrium with the dynamin 1 (G767T) allele, wherein detection of the dynamin 1 (G767T) allele or allele in linkage disequilibrium with dynamin 1 (G767T) allele is indicative that the dog has or is predisposed to the development of EIC, and (c) providing results regarding whether the dog has an EIC associated allele.

The term "biomarker" is generally defined herein as a biological indicator, such as a particular molecular feature, that may affect or be related to diagnosing or predicting an individual's health. For example, in certain embodiments of the present invention, the biomarker comprises a mutant canine DNM1 gene, such as a polymorphic allele of DNM1 having a thymine (T) nucleotide at position 767 of SEQ ID NO:1, a cytosine (C) or T nucleotide at position 603, a C or T nucleotide at position 633, an adenine (A) or guanine (G) nucleotide at position 1827, and/or a C or T nucleotide at position 759. The DNM1 gene that has a T at position 767 encodes a protein having an R (arginine) to L (leucine) substitution at amino acid residue 256.

"Oligonucleotide probe" can refer to a nucleic acid segment, such as a primer, that is useful to amplify a sequence in the DNM1 gene that is complementary to, and hybridizes specifically to, a particular sequence in DNM1, or to a nucleic acid region that flanks DNM1.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

In one embodiment of the present invention, the method also involves contacting the sample with at least one oligonucleotide probe to form a hybridized nucleic acid and amplifying the hybridized nucleic acid. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. For example, in certain embodiments of the present invention, the DNM1 gene, or a portion thereof, may be amplified by PCR. In another embodiment of the present invention, at least one oligonucleotide probe is immobilized on a solid surface.

The methods of the present invention can be used to detect the presence of a biomarker associated with canine Exercise Induced Collapse (EIC) in a dog such as a puppy, one of a breeding pair of dogs, or any dog at any stage of life.

Further provided by the present invention is a method for diagnosing Exercise Induced Collapse (EIC) in a dog, the method involving obtaining a physiological sample from the dog, wherein the sample comprises nucleic acid; and detecting the presence of a biomarker in the sample, wherein the presence of the biomarker is indicative of the disease. One embodiment of the method further involves contacting the sample with at least one oligonucleotide probe to form a hybridized nucleic acid and amplifying the hybridized nucleic acid. For example, in one embodiment, the DNM1 gene or a portion thereof is amplified, for example, by polymerase chain reaction, strand displacement amplification, ligase chain reaction, amplification methods based on the use of Q-beta replicase, and/or nucleic acid sequence-based amplification. In one embodiment of the method, the biomarker contains a DNM1 gene having a G to T substitution at nucleotide 767, or a gene encoding a protein having an R to L substitution at amino acid residue 256. The method can be used to detect EIC in a dog.

Further provided by the present invention is a kit comprising a diagnostic test for detecting the presence of canine EIC in a dog comprising packaging material, containing, separately packaged, at least one oligonucleotide probe capable of forming a hybridized nucleic acid with DNM1 and instructions means directing the use of the probe in accord with the methods of the invention. In certain embodiments, the kit containing a second primer oligonucleotide that hybridizes either 3' or 5' respectively to the allele, so that the allele can be amplified. In certain embodiments, the first primer and the second primer hybridize to a region in the range of between about 50 and about 1000 base pairs. In certain embodiments, the kit additionally contains a detection means. In certain embodiments, the kit additionally includes an amplification means.

Other features and advantages of the invention will be apparent from the following detailed description and claims.

BRIEF DESCRIPTION OF DRAWINGS

FIG. 1. This canine DNM1 long form coding DNA sequence contains 2595 bases (SEQ ID NO:1). The dynamin 1 protein predicted from this DNA sequence contains 864 amino acids and a molecular weight of 97,383. Four single nucleotide polymorphisms (SNPs) within the DNM1 coding DNA sequence were found in the 2 affected and 2 control dogs sequenced in entirety (indicated in bold and underlined).

Figure 4:
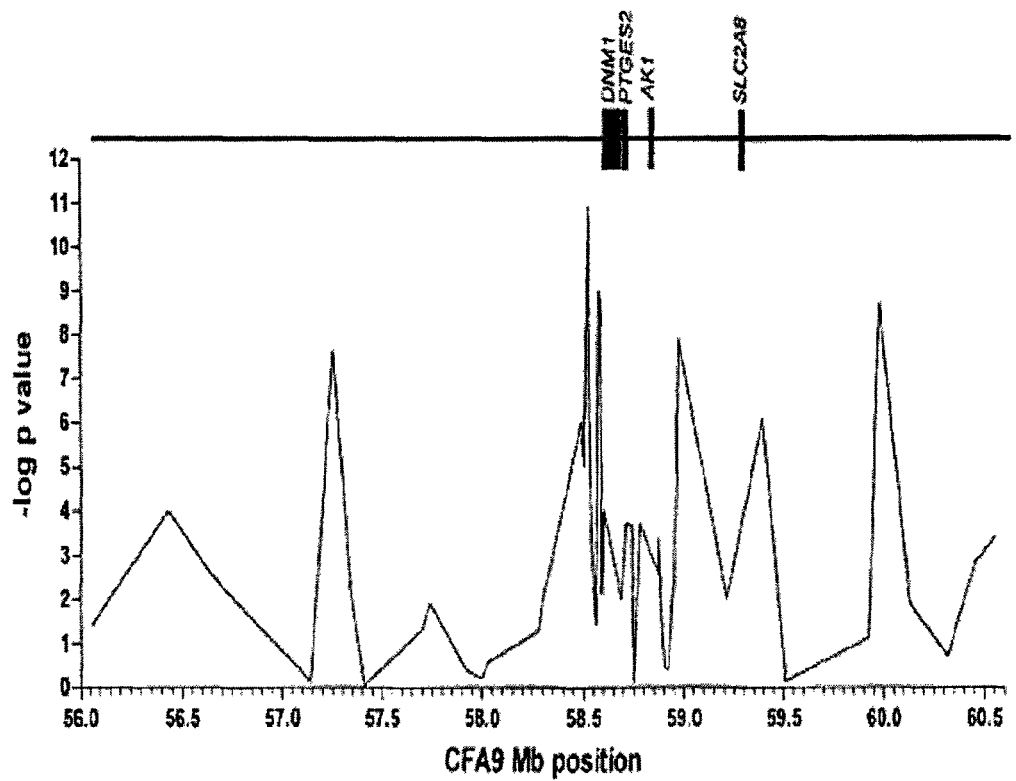

Two exon 5 SNPs, C or T (i.e., Y) at coding nucleotide position 603, and C or T (i.e., Y) at coding nucleotide position 633, were synonymous at codons 201 and 211 respectively. One exon 6 SNP, C or T (i.e., Y) at coding nucleotide position 759 was synonymous at codon 253. However, an exon 6 G to T substitution at coding nucleotide position 767 resulted in the conversion of codon 256 from arginine to leucine (R256L mutation). Affected dogs are homozygous for the T767 allele, while the control dogs were heterozygous or homozygous for the G767 allele.

FIG. 2. Amino acid sequence predicted from the DNM1 long form coding DNA sequence in FIG. 1 (SEQ ID NO:2). The first three SNPs were synonymous at codons 201, 211 and 253 respectively, as they did not change the resultant amino acid sequence (indicated in bold and underlined). However, the G767T SNP changed the amino acid at codon 256 from an R to an L.

FIG. 3. Species alignment of the control canine and human dynamin 1 amino acid sequences in the region of the R256L mutation reveals a remarkable cross-species and cross-gene conservation. This conservation was shared by the other dynamin gene family members (dynamin 2 and dynamin 3). Sequences were obtained from the following accession numbers: Dog DNM1, this study; Human DNM1, NP_004399.2; Human DNM2, NP_001005360; Human DNM3, NP_056384.2; Mouse DNM1, NP_034195.2; Mouse DNM2, NP_001034609.1; Mouse DNM3, NP_001033708.1; Bovine DNM1, NP_001092839.1; Chicken, XP_001233250.1; Danio rerio, NP_001025299.1; Drosophila, NP_727910.1. Underlined sequences are conserved across species or gene families in that group. The Arg256Leu mutation associated with EIC is highlighted. FIG. 3 discloses SEQ ID NOS 3-5, 126, 127, 6-9, 3, 10-11 and 124-125, respectively, in order of appearance.

FIG. 4. CFA9 SNP Association Analysis with EIC. SNP genotypes from canine chromosome 9 were obtained. Chi square statistics comparing allele and genotype frequencies were performed for 55 affected and 37 control dogs that comprised the subset of maximally unrelated individuals.

FIG. 5A. Canine Dynamin 1 (DNM1) short form coding DNA sequence and polymorphisms (SEQ ID NO:12). CDS SNPs identified within the study dogs, or between the study dogs and CanFam 2.0, are highlighted. The nonsynonymous G767T DNM1 SNP highly associated with EIC, and responsible for the R256L mutation, is also underlined and bolded. FIG. 5B. Canine DNM1 short form amino acid sequence. Residues in which synonymous SNPs in the CDS were found are highlighted. The R256L mutation highly associated with EIC is also underlined and bolded (SEQ ID NO:13).

Figure 6:
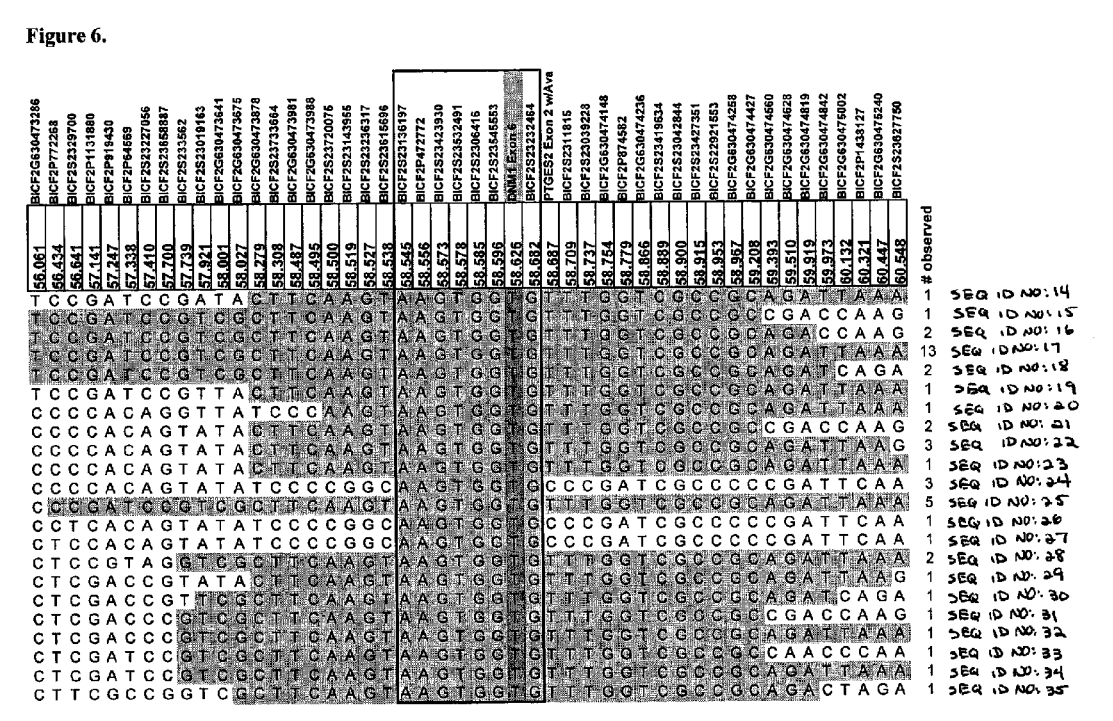

FIG. 6. Shared SNP Haplyotypes of 23 affected dogs (SEQ ID NOS:14-35). SNPs were genotyped and PHASED. Haplotypes were generated on 23 affected dogs as described in Materials and Methods. These 23 dogs fit the criteria for presumed affected, had 5 or more episodes of collapse, and at least one year of no other known medical problems since the episodes first occurred. The number of observations of each haplotype is indicated in the right most column. The region of conservation of each haplotype relative to the longest most common haplotype is highlighted in yellow. The G767T DNM1 mutation is in orange.

FIGS. 7A-7J. Exons are capitalized, Introns in lower case. SNPs are underlined. FIG. 7A. DNM1 exon primers and product sequence. Exons 1-4. (SEQ ID NOS:36-47). FIG. 7B. Predicted DNM1 exon sequence and polymorphisms. Exons 1-4. (SEQ ID NOS:48-51). FIG. 7C. DNM1 exon primers and product sequence. Exons 5-9. (SEQ ID NOS:52-57). FIG. 7D. Predicted DNM1 exon sequence and polymorphisms. Exons 5-9. (SEQ ID NOS:58-62). FIG. 7E. DNM1 exon primers and product sequence. Exons 10-14. (SEQ ID NOS: 63-74). FIG. 7F. Predicted DNM1 exon sequence and polymorphisms. Exons 10-14. (SEQ ID NOS:75-79). FIG. 7G. DNM1 exon primers and product sequence. Exons 15-19. (SEQ ID NOS: 80-94). FIG. 7H. Predicted DNM1 exon sequence and polymorphisms. Exons 15-19. (SEQ ID NOS: 95-100). FIG. 7I. DNM1 exon primers and product sequence. Exons 20-22 and Exon 6 for genotyping. (SEQ ID NOS:101-115). FIG. 7J. Predicted DNM1 exon sequence and polymorphisms. Exons 20-21 and Exon 6 for genotyping. (SEQ ID NOS:116-119).

Figures 8A, 8B, 8C:
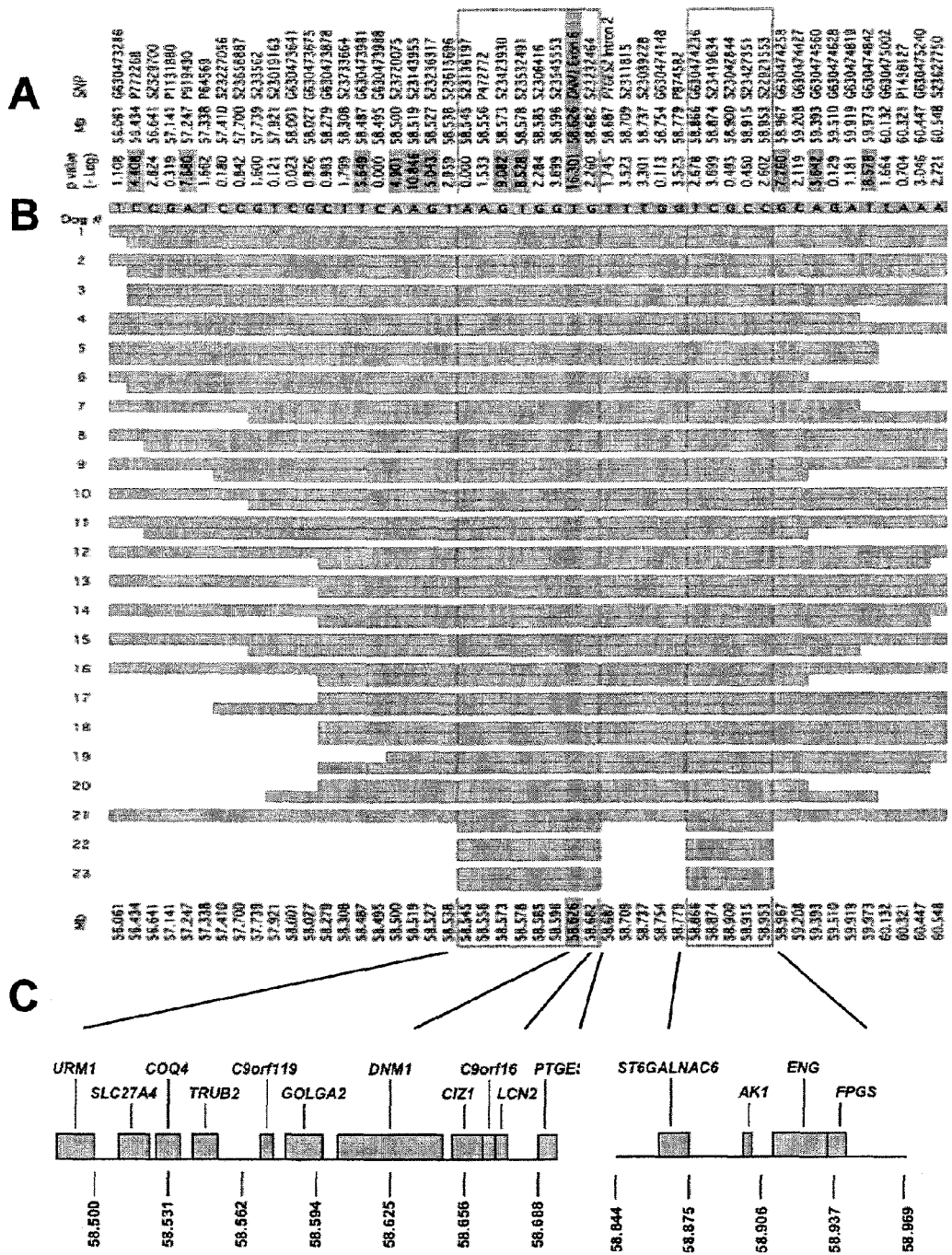

FIGS. 8A-8C. SNP association analysis, haplotypes and genes from the region of CFA9 genetically linked to EIC. SNP genotypes were obtained and haplotypes derived as described in the Materials and Methods. FIG. 8A. Abbreviated SNP ID's and positions in Mb are shown across the top row. Chi-square statistics comparing allele and genotype frequencies were performed for 56 presumed EIC affected and 38 unaffected dogs that comprised the subset of maximally unrelated individuals. The negative log of the p-value of the chi-square results is shown. P-values $<10^{-04}$ (i.e., $-\log >4.00$) are highlighted. FIG. 8B. SNP genotypes in the longest and most common EIC haplotype observed are indicated in the top row. Both haplotypes from 23 dogs with the strongest evidence of EIC follow. The regions of conservation of each haplotype relative to the longest most common haplotype are provided as horizontal bars for each individual chromosome. These dogs all had 5 or more episodes of collapse, and at least one year of no other known medical problems since the episodes first occurred. The 137 Kb and 87 Kb minimally conserved blocks of homozygosity are outlined vertically. Individuals 21-23 have conserved homozygosity limited to these 137 and 87 Kb blocks. The G767T mutation subsequently found in the DNM1 gene (SEQ ID NO: 128) is highlighted. FIG. 8C. CFA9 Mb positions of the ENSEMBL annotated genes in the 137 Kb and 87 Kb blocks.

FIG. 9 provides a list of known genes in the region in linkage disequilibrium with DNM1. The known genes include ubiquitin related modifier 1 (URM), fatty acid transporter 4 (SLC27A4), coenzyme Q4 homolog (COQ4), tRNA pseudouridin synthase 2 (TRUB2), Chromosome 9 open reading frame 119 (COorf119), Golgi autoantigen, golgin subfamily a, 2 (GOLGA2), Dynamin 1 (DNM1), CDKN1A interacting zinc finger protein 1 (CIZ1), hypothetical protein C90rf16 (C9orf16), and Lipcalin 2 (LCN2).

DETAILED DESCRIPTION OF THE INVENTION

Genotype Screening

Traditional methods for the screening of heritable diseases have depended on either the identification of abnormal gene products (e.g., sickle cell anemia) or an abnormal phenotype (e.g., mental retardation). With the development of simple and inexpensive genetic screening methodology, it is now possible to identify polymorphisms that indicate a propensity to develop disease, even when the disease is of polygenic origin.

Genetic screening (also called genotyping or molecular screening), can be broadly defined as testing to determine if a patient has mutations (or alleles or polymorphisms) that either cause a disease state or are "linked" to the mutation causing a disease state. Linkage refers to the phenomenon that DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a haplotype which spans or is linked to a disease-causing mutational change, serves as a predictive measure of an individual's likelihood of having inherited that disease-causing mutation. Such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases.

The statistical correlation between a disorder and a polymorphism does not necessarily indicate that the polymorphism directly causes the disorder. Rather the correlated polymorphism may be a benign allelic variant which is linked to (i.e., in linkage disequilibrium with) a disorder-causing mutation which has occurred in the recent evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. A broad-spanning haplotype (describing the typical pattern of co-inheritance of alleles of a set of linked polymorphic markers) can be targeted for diagnostic purposes once an association has been drawn between a particular disease or condition and a corresponding haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

The inventors identified multi-generation pedigrees of Labrador Retrievers affected with EIC and performed a genome scan with approximately 500 microsatellite DNA markers. A locus for the EIC gene on canine chromosome 9 was identified based on a maximum LOD score of 12.2. Haplotype analysis with SNP markers in this region confirmed the locus and narrowed the interval containing the EIC gene to <250 Kb. Four positional candidate genes in this region (DNM1, PTGES2, AK1 and SLC2A8) were analyzed for possible mutations in several control and EIC-affected dogs. The PTGES2, AK1 and SLC2A8 genes were ruled out, however a G to T nucleotide mutation at position 767 of the DNM1 gene was identified (FIG. 1). This mutation causes the normal arginine amino acid residue at codon 256 of the dynamin 1 protein to be replaced with a leucine residue (FIG. 2). This EIC DNM1 gene mutation will be referred to as G767T in the coding nucleotide sequence, resulting in the dynamin 1 amino acid Arg256Leu or R256L mutation. The alleles are thus G767 and T767 when referring to the DNM1 coding DNA sequence and Arg256 and Leu256 when referring to the dynamin 1 amino acid sequence, and the alleles associated with EIC are the T767 DNA and L256 protein alleles.

Alignment of the control canine and human full length dynamin 1 amino acid sequences reveals remarkable cross-species conservation. 860 of the 864 amino acids were identical, and of these four differences only two (Q to H at codon 128, and A to T at codon 511) were non-conservative substitutions. Amino acid sequence alignment of the 241-270 residue segment of the canine DNM1 across multiple species and the other two dynamin gene family members (DNM2 and DNM3) also reveals a high level of conservation (FIG. 3). Vertebrate DNM1 amino acid residues 250-263 are identical, and Drosophila residues 251-263 and *C. elegans* residues 254-259 are identical to the vertebrate sequences. Mammalian DNM1 is also identical to the DNM2 and DNM3 isoforms at amino acid residues 254-263. This combined sequence data indicated that the R256L DNM1 amino acid substitution was a very strong candidate EIC mutation to pursue further in a larger sample population.

Six different categories of Labrador Retriever dogs submitted for the collapse study were formed based on the available medical and questionnaire information. They are the following:

Group 1. Presumed affected. Dogs with a history of more than one collapse episode in which the back legs became weak first and became flaccid. These episodes were without pain, and the dogs had no detectable metabolic, respiratory, heart, muscle, or orthopedic problems based on veterinary examination and screening blood work.

Group 2. Recurrent collapse. Dogs with incomplete description of the collapse episodes.

Group 3. Single Collapse Episode. These dogs otherwise met the criteria for presumed affected.

Group 4. Atypical collapse. Dogs with recurrent episodes of collapse, however the description did not entirely match with the criteria for classification of presumed affected.

Group 5. Alternative Collapse. Dogs for which another potential underlying cause of collapse was identified.

Group 6. No Collapse. These dogs were never observed to collapse.

Table 2 in Example 1 below presents the frequency of the three DNM1 genotypes in Labrador Retrievers that met the different classification criteria. 97% of dogs presumed affected, and 88% of dogs with collapse but incomplete documentation, were homozygous for the T767 allele. Dogs in which the likelihood of truly having EIC was lower (single reported collapse, atypical collapse, or another potential cause identified) had a decreasing likelihood of being homozygous for the T767 allele (62%, 43%, and 20% respectively) Almost a dozen dogs that collapsed only once or had collapse episodes that were less typical or completely described were heterozygotes. 9% of dogs for which the owners reported no episodes of collapse were homozygous for the T767 allele associated with EIC, while 49% were heterozygous, and 42% were homozygous for the G767 allele.

Thirty-five parents of T767 homozygous dogs were available to genotype. Twenty-nine of these parents were heterozygous and had no reports of collapse. Six of these parents were homozygous T767 themselves; four of them had reports of collapse and the other 2 may not have been subjected to conditions to cause a collapse. This data, and the fact that most dogs that collapse are T/T, is indicative of an autosomal recessive trait. However, that 9% of dogs that were not reported to collapse were also T/T indicates that the trait may not be completely penetrant or that genetically susceptible dogs do not collapse until they are exposed to extreme conditions (exercise and excitement) sufficient to initiate collapse. That 12 of 89 (13%) of G/T dog did experience some form of collapse (usually atypical or a single episode) could indicate either partial dominance or another disorder causing collapse. Lastly, that a number of dogs that experience a collapse have the G/G genotype indicates that other collapse phenotypes attributable to other causes do exist.

This G767T DNM1 polymorphism is a compelling candidate causal mutation for EIC due to the critical function of dynamin in synaptic transmission in the central nervous system and the strong evolutionary conservation across species. According to NCBI, this gene encodes a member of the dynamin subfamily of GTP-binding proteins. The encoded protein possesses unique mechanochemical properties used to tubulate and sever membranes, and is involved in clathrin-mediated endocytosis and other vesicular trafficking processes. Mice in which the DNM1 gene has been knocked out are not viable and their neurons exhibit a loss of activity upon repeated stimulation. In addition a number of phenotypes have been observed in *Drosophila* and *C. elegans* carrying mutations in the homologous genes.

DNA testing enables veterinarians, owners, trainers, and breeders to more accurately determine if a dog with clinical signs of EIC has the heritable and "classic" form of disease that can be specifically attributed to this DNM1 gene mutation. All that is needed are a tissue sample containing the individual's DNA (typically cheek swab or blood) and appropriate PCR and sequence analysis technology to detect the G to T single nucleotide change.

Also, DNA testing enables owners and breeders to determine if any dog, whether they show signs of EIC or not, can be expected to produce offspring with EIC. 100% of the puppies produced by the mating of two T/T dogs would be susceptible to EIC. 50% of the puppies produced by the mating of a T/T dog with a heterozygote would be susceptible and 50% would be heterozygotes. 25% of the puppies produced by the mating of two heterozygotes would be susceptible, and 50% would be heterozygotes. Breeding programs could incorporate this information in the selection of parents that could reduce or prevent the production of homozygous affecteds, which are susceptible to EIC, and eventually reduce and potentially even eliminate EIC.

The current diagnosis of EIC in dogs by veterinarians requires a standardized retrieving exercise test, but is more often based on signs of collapse reported during training or competition in the field. Since there are varying environmental and "excitement" conditions in the field, and different dogs may collapse under slightly different conditions, these are not highly reliable diagnoses. It is worth noting that EIC is an entirely different condition than another heritable and prevalent neuromusucular disease in Labrador Retrievers known as central nuclear myopathy or CNM.

The inventors are studying the frequency of the DNM1 mutation in retrievers and other breeds (Table 3). These dogs were obtained from field trial competitions in the upper Midwest and came from 20 different states and three Canadian provinces. At this time it is known that almost 5% of all Labrador Retrievers participating in these field trials are homozygous and 39% are carriers. This reflects a strong founder effect of champion dogs that have sired and grand-sired a large fraction of the population. However, the incidence of the DNM1 mutation in other sub-populations that likely comprise the majority of all Labrador Retrievers in the US is not known. The DNM1 mutation is also present in likely variable extents in other retrieving breeds, including Chesapeake Bay and Curly-Coated Retrievers, as well as Border Collies.

Definitions

The term "allele" refers to the different sequence variants found at different polymorphic regions. The sequence variants may be single or multiple base changes, including without limitation insertions, deletions, or substitutions, or may be a variable number of sequence repeats. For example, the present invention relates, inter alia, to the discovery that an allele of the DNM1 gene is associated with EIC in dogs. A "DNM1 allele" refers to a normal allele of the DNM1 locus as well as an allele carrying a variation(s) that predispose a dog to develop EIC. The coexistence of multiple alleles at a locus is known as "genetic polymorphism." Any site at which multiple alleles exist as stable components of the population is by definition "polymorphic." An allele is defined as polymorphic if it is present at a frequency of at least 1% in the population. A "single nucleotide polymorphism (SNP)" is a DNA sequence variation that involves a change in a single nucleotide.

"Biological activity" or "bioactivity" or "activity" or "biological function", which are used interchangeably, for the purposes herein means an effector or antigenic function that is directly or indirectly performed by an DNM1 polypeptide (whether in its native or denatured conformation), or by any subsequence thereof Biological activities include binding to a target peptide, e.g., an receptor. A DNM1 bioactivity can be modulated by directly affecting a DNM1 polypeptide. Alternatively, DNM1 bioactivity can be modulated by modulating the level of a DNM1 polypeptide, such as by modulating expression of a DNM1 gene.

As used herein the term "bioactive fragment of a DNM1 polypeptide" refers to a fragment of a full-length DNM1 polypeptide, wherein the fragment specifically mimics or antagonizes the activity of a wild-type DNM1 polypeptide.

The term "an aberrant activity," as applied to an activity of a polypeptide such as DNM1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant DNM1 activity due to over-expression or under-expression of a DNM1 locus gene encoding a DNM1 locus polypeptide.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, in certain embodiments, the control sample comprises the material to be tested. However, where the sample to be tested is genomic DNA, the control sample is preferably a highly purified sample of genomic DNA.

"Genotyping" refers to the analysis of an individual's genomic DNA (or a nucleic acid corresponding thereto) to identify a particular disease causing or contributing mutation or polymorphism, directly or based on detection of a mutation or polymorphism (a marker) that is in linkage disequilibrium with the disease causing or contributing gene.

The term "haplotype" as used herein is intended to refer to a set of alleles that are inherited together as a group (are in linkage disequilibrium) at statistically significant levels ($p_{corr}$<0.05). As used herein, the phrase "an DNM1 haplotype" refers to a haplotype in the DNM1 loci.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium." The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene." A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (e.g., exercise induced collapse). The alleles are thus over-represented in frequency in individuals with disease as compared to healthy individuals. Thus, these alleles can be used to predict disease even in pre-symptomatic or pre-diseased individuals.

As used herein, the term "specifically hybridizes" or "specifically detects" refers to the ability of a nucleic acid molecule to hybridize to at least approximately six consecutive nucleotides of a sample nucleic acid.

The terms "protein," "peptide" and "polypeptide" are used interchangeably herein.

The invention encompasses isolated or substantially purified nucleic acid molecules. In the context of the present invention, an "isolated" or "purified" DNA molecule is a DNA molecule that, by human intervention, exists apart from its native environment and is therefore not a product of nature. An isolated DNA molecule may exist in a purified form or may exist in a non-native environment. For example, an "isolated" or "purified" nucleic acid molecule, or portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences and proteins or partial-length proteins encoded thereby are also encompassed by the present invention.

By "fragment" or "portion" of a sequence is meant a full length or less than full length of the nucleotide sequence encoding, or the amino acid sequence of a polypeptide or protein. As it relates to a nucleic acid molecule, sequence or segment of the invention when linked to other sequences for expression, "portion" or "fragment" means a sequence having, for example, at least 80 nucleotides, at least 150 nucleotides, or at least 400 nucleotides. If not employed for expressing, a "portion" or "fragment" means, for example, at least 9, 12, 15, or at least 20, consecutive nucleotides, e.g., probes and primers (oligonucleotides), corresponding to the nucleotide sequence of the nucleic acid molecules of the invention. Alternatively, fragments or portions of a nucleotide sequence that are useful as hybridization probes generally do not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides or more.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Synthetic" polynucleotides are those prepared by chemical synthesis.

"Recombinant DNA molecule" is a combination of DNA sequences that are joined together using recombinant DNA technology and procedures used to join together DNA sequences as described, for example, in Sambrook and Russell (2001).

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, such as dynamin 1, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

A "mutant" dynamin 1 (DMN1) refers to the protein or fragment thereof that is encoded by a DAM1 gene having a mutation, e.g., such as might occur at the DMN1 locus. Mutations in DMN1 may be disease-causing in a dog heterozygous for the mutant DMN1 allele, e.g., a dog heterozygous for a mutation leading to a mutant gene product such as a substitution mutation of DMN1, such as that designated herein as G767T.

"Somatic mutations" are those that occur only in certain tissues, e.g., in liver tissue, and are not inherited in the germline. "Germline" mutations can be found in any of a body's tissues and are inherited. The present DAM1 mutation is a germline mutation.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, or at least 80%, 90%, or even at least 95%.

Another indication that nucleotide sequences are substantially identical is if two molecules hybridize to each other under stringent conditions (see below). Generally, stringent conditions are selected to be about 5° C. lower than the thermal melting point $(T_m)$ for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%; at least 80%, 81%, 82%, 83%, 84%, 85%, 86%, 87%, 88%, or 89%; or at least 90%, 91%, 92%, 93%, or 94%; or even at least 95%, 96%, 97%, 98% or 99% sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m\ 81.5°\ C.+16.6\ (\log M)+0.41\ (\%\ GC)-0.61\ (\%\ \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. Guidance as to appropriate amino acid substitutions that do not affect biological activity of the protein of interest are well known in the art. Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally-occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations."

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

A "host cell" is a cell which has been transformed, or is capable of transformation, by an exogenous nucleic acid molecule. Thus, "transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically includes sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will have the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified through, for example, the use of single-stranded mutagenesis. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Genome" refers to the complete genetic material of an organism.

"Coding sequence" refers to a DNA or RNA sequence that codes for a specific amino acid sequence and excludes the non-coding sequences. For example, a DNA "coding sequence" or a "sequence encoding" a particular polypeptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. It may constitute an "uninterrupted coding sequence," i.e., lacking an intron, such as in a cDNA or it may include one or more introns bounded by appropriate splice junctions. An "intron" is a sequence of RNA that is contained in the primary transcript but that is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

The term "regulatory sequence" is art-recognized and intended to include promoters, enhancers and other expression control elements (e.g., polyadenylation signals). Such regulatory sequences are known to those skilled in the art. It should be understood that the design of the expression vector may depend on such factors as the choice of the host cell to be transfected and/or the amount of fusion protein to be expressed.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

A control element, such as a promoter, "directs the transcription" of a coding sequence in a cell when RNA polymerase binds the promoter and transcribes the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

"Operably-linked" refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" or "translation stop codon" or "stop codon" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. The change of at least one nucleotide in a nucleic acid sequence can result in an interruption of the coding sequence of the gene, e.g., a premature stop codon. Such sequence changes can cause a mutation in the polypeptide encoded by a DNM1 gene.

Prognostic Assays and Kits

The invention is based, at least in part, on the findings, which are described in detail in the following examples, that the DNM1 (G767T) is significantly associated with the development of exercise induced collapase. The present invention, therefore, provides methods and kits for determining whether a subject has or is likely to develop EIC.

In addition to the allelic patterns described above, as described herein, one of skill in the art can readily identify other alleles (including polymorphisms and mutations) that are in linkage disequilibrium with an allele associated with EIC. For example, a nucleic acid sample from a first group of subjects without a particular disorder can be collected, as well as DNA from a second group of subjects with the disorder. The nucleic acid sample can then be compared to identify those alleles that are over-represented in the second group as compared with the first group, wherein such alleles are presumably associated with a disorder. Alternatively, alleles that are in linkage disequilibrium with an allele that is associated with the disorder can be identified, for example, by genotyping a large population and performing statistical analysis to determine which alleles appear more commonly together than expected. The group may be chosen to be comprised of genetically related individuals. Genetically related individuals include individuals from the same breed, or even the same family. As the degree of genetic relatedness between a control group and a test group increases, so does the predictive value of polymorphic alleles that are ever more distantly linked to a disease-causing allele. This is due to the fact that less evolutionary time has passed to allow polymorphisms which are linked along a chromosome in a founder population to redistribute through genetic cross-over events. Thus breed-specific, and even family-specific diagnostic genotyping assays can be developed to allow for the detection of disease alleles which arose at ever more recent times in canine evolution.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inherited. Thus, for individuals related by common breed or family, the reliability of ever more distantly spaced polymorphic loci can be relied upon as an indicator of inheritance of a linked disease-causing mutation.

In another embodiment, the method of the invention may be employed by detecting the presence of an DNM1 associated polymorphism that is in linkage disequilibrium with one or more predictive alleles. Alleles of the DNM1 haplotype are known to be in linkage disequilibrium are the genes and intergenic regions between 58.545 and 58.682 MB position on canine chromosome 9, according to the current assembly of the canine genome sequence termed "canFam2." For example, see the genes shown in FIGS. 8A-8C and FIG. 9.

Appropriate probes may be designed to hybridize to a specific gene of the DNM1 locus. Alternatively, these probes may incorporate other regions of the relevant genomic locus, including intergenic sequences. Yet other polymorphisms available for use with the immediate invention are obtainable from various public sources. From such sources SNPs as well as other canine polymorphisms may be found.

Accordingly, the nucleotide segments of the invention may be used for their ability to selectively form duplex molecules with complementary stretches of canine chromosomes or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M-0.15M NaCl at temperatures of about 50° C. to about 70° C. Such selective conditions may tolerate little, if any, mismatch between the probe and the template or target strand.

Other alleles or other indicia of a disorder can be detected or monitored in a subject in conjunction with detection of the alleles described above.

Many methods are available for detecting specific alleles at canine polymorphic loci. Certain methods for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

Nucleic Acids of the Invention

Sources of nucleotide sequences from which the present nucleic acid molecules can be obtained include any prokaryotic or eukaryotic source. For example, they can be obtained from a mammalian, such as a canine, cellular source. Alternatively, nucleic acid molecules of the present invention can be obtained from a library.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule that is complementary or hybridizes to a sequence in a gene of interest, i.e., a nucleic acid sequence encoding dynamin 1 (DNM1), and remains stably bound under stringent conditions (as defined by methods well known in the art). Thus, the RNA or DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from the source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Nucleic Acid Amplification Methods

According to the methods of the present invention, the amplification of DNA present in a physiological sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Various labels that can be incorporated into or operably linked to nucleic acids are well known in the art, such as radioactive, enzymatic, and florescent labels. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In one embodiment of the invention, the DNM1 gene is amplified by PCR using primers based on the known sequence. The amplified gene is then sequenced using automated sequencers. In this manner, the DNM1 gene from dogs suspected of having EIC in their pedigree are sequenced until a mutation is found. For example, one mutation is the G to T substitution at nucleotide base 767.

According to the diagnostic method of the present invention, alteration within the wild-type DNM1 locus is detected. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Point mutational events may occur in regulatory regions, such as in the promoter of the gene, leading to loss or diminution of expression of the mRNA. Point mutations may also abolish proper RNA processing, leading to loss of expression of the DNM1 gene product, or to a decrease in mRNA stability or translation efficiency. EIC is a disease caused by a point mutation at nucleic acid 767. While most dogs predisposed to EIC have two mutated alleles, a few dogs with a collapse syndrome resembling EIC have only one mutated allele.

Diagnostic techniques that are useful in the methods of the invention include, but are not limited to direct DNA sequencing, PFGE analysis, allele-specific oligonucleotide (ASO), dot blot analysis and denaturing gradient gel electrophoresis, and are well known to the artisan.

There are several methods that can be used to detect DNA sequence variation. Direct DNA sequencing, either manual sequencing or automated fluorescent sequencing can detect sequence variation. Another approach is the single-stranded conformation polymorphism assay (SSCA). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA) and chemical mismatch cleavage (CMC). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result.

Detection of point mutations may be accomplished by molecular cloning of the DNM1 allele(s) and sequencing the allele(s) using techniques well known in the art. Alternatively, the gene sequences can be amplified directly from a genomic DNA preparation from canine tissue, using known techniques. The DNA sequence of the amplified sequences can then be determined.

There are six well known methods for a more complete, yet still indirect, test for confirming the presence of a mutant allele: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. For allele-specific PCR, primers are used which hybridize at their 3' ends to a particular DNM1 mutation. If the particular mutation is not present, an amplification product is not observed. Amplification Refractory Mutation System (ARMS) can also be used. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as known in the art can be used.

In the first three methods (SSCA, DGGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe that is complementary to the dog wild-type DNM1 gene coding sequence. The riboprobe and either mRNA or DNA isolated from the tumor tissue are annealed (hybridized) together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the DNM1 mRNA or gene but can be a segment of either. If the riboprobe comprises only a segment of the DNM1 mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR before hybridization.

Nucleic acid analysis via microchip technology is also applicable to the present invention.

DNA sequences of the DNM1 gene that have been amplified by use of PCR may also be screened using allele-specific probes. These probes are nucleic acid oligomers, each of which contains a region of the DNM1 gene sequence harboring a known mutation. For example, one oligomer may be about 30 nucleotides in length, corresponding to a portion of the DNM1 gene sequence. By use of a battery of such allele-specific probes, PCR amplification products can be screened to identify the presence of a previously identified mutation in the DNM1 gene. Hybridization of allele-specific probes with amplified DNM1 sequences can be performed, for example, on a nylon filter. Hybridization to a particular probe under stringent hybridization conditions indicates the presence of the same mutation in the tissue as in the allele-specific probe.

Alteration of DNM1 mRNA expression can be detected by any technique known in the art. These include Northern blot analysis, PCR amplification and RNase protection. Diminished mRNA expression indicates an alteration of the wild-type DNM1 gene.

Alteration of wild-type DNM1 genes can also be detected by screening for alteration of wild-type DNM1 protein, or a portion of the DNM1 protein. For example, monoclonal antibodies immunoreactive with DNM1 (or to a specific portion of the DNM1 protein) can be used to screen a tissue. Lack of cognate antigen would indicate a mutation. Antibodies specific for products of mutant alleles could also be used to detect mutant DNM1 gene product. Such immunological assays can be done in any convenient formats known in the art. These include Western blots, immunohistochemical assays and ELISA assays. Any means for detecting an altered DNM1 protein can be used to detect alteration of wild-type DNM1 genes. Functional assays, such as protein binding determinations, can be used. In addition, assays can be used that detect DNM1 biochemical function. Finding a mutant DNM1 gene product indicates alteration of a wild-type DNM1 gene.

Mutant DNM1 genes or gene products can be detected in a variety of physiological samples collected from a dog. For example, a physiological sample can be a sample collected from an individual dog, such as including, but not limited to, e.g., a cell sample, such as a blood cell, e.g., a lymphocyte, a peripheral blood cell; a tissue sample such as mucosal sample (e.g., cheek swab) or muscle tissue, e.g., skeletal muscle; an organ sample, e.g., liver or skin; a hair sample, e.g., a hair sample with roots; and/or a fluid sample, such as blood.

The methods of diagnosis of the present invention are applicable to any canine disease in which DNM1 has a role. The diagnostic method of the present invention is useful, for example, for veterinarians, Breed Associations, or individual breeders, so they can decide upon an appropriate course of treatment, and/or to determine if an animal is a suitable candidate for breeding.

Oligonucleotide Probes

As noted above, the method of the present invention is useful for detecting the presence of a polymorphism in canine DNA, in particular, the presence of a G to T nucleotide substitution at position 767 in the coding sequence of canine DNM1 (SEQ ID NO:1). This substitution results in the replacement of an arginine (R) amino acid at codon 256 by a histidine (L) in the dynamin 1 protein (SEQ ID NO:2).

Primer pairs are useful for determination of the nucleotide sequence of a particular DNM1 allele using PCR. The pairs of single-stranded DNA primers can be annealed to sequences within or surrounding the DNM1 gene in order to prime amplifying DNA synthesis of the DNM1 gene itself. A complete set of these primers allows synthesis of all of the nucleotides of the DNM1 coding sequences, i.e., the exons. The set of primers preferably allows synthesis of both intron and exon sequences. Allele-specific primers can also be used. Such primers anneal only to particular DNM1 mutant alleles, and thus will only amplify a product in the presence of the mutant allele as a template.

The first step of the process involves contacting a physiological sample obtained from a dog, which sample contains nucleic acid, with an oligonucleotide probe to form a hybridized DNA. The oligonucleotide probes that are useful in the methods of the present invention can be any probe comprised of between about 4 or 6 bases up to about 80 or 100 bases or more. In one embodiment of the present invention, the probes are between about 10 and about 20 bases.

The primers themselves can be synthesized using techniques that are well known in the art. Generally, the primers can be made using oligonucleotide synthesizing machines that are commercially available. Given the sequence of the DNM1 coding sequence as set forth in SEQ ID NO:1, design of particular primers is well within the skill of the art.

Oligonucleotide probes may be prepared having any of a wide variety of base sequences according to techniques that are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 7-deaza-guanine 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylamninomethyluridine, 5-methoxyaminomethyl-2-thiouridine, β,D-mannosylqueosine, 5-methloxycarbonylmethyluridine, 5-methoxyuridine, 2-methyltio-N6-isopentenyladenosine, N-((9-β-D-ribofuranosyl-2-methylthiopurine-6-yl)carbamoypthreonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-Methylurdine, N-((9-beta-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonotlioates, phosphoroinorpholidates, phosphoropiperazidates and phosplioramidates (for example, every other one of the internucleotide bridging phosphate residues may be modified as described). The oligonucleotide may be a "peptide nucleic acid" such as described in Nielsen et al., *Science*, 254, 1497-1500 (1991).

The only requirement is that the oligonucleotide probe should possess a sequence at least a portion of which is capable of binding to a known portion of the sequence of the DNA sample.

It may be desirable in some applications to contact the DNA sample with a number of oligonucleotide probes having different base sequences (e.g., where there are two or more target nucleic acids in the sample, or where a single target nucleic acid is hybridized to two or more probes in a "sandwich" assay).

The nucleic acid probes provided by the present invention are useful for a number of purposes. The probes can be used to detect PCR amplification products. They may also be used to detect mismatches with the DNM1 gene or mRNA using other techniques.

Hybridization Methodology

The DNA (or nucleic acid) sample may be contacted with the oligonucleotide probe in any suitable manner known to those skilled in the art. For example, the DNA sample may be solubilized in solution, and contacted with the oligonucleotide probe by solubilizing the oligonucleotide probe in solution with the DNA sample under conditions that permit hybridization. Suitable conditions are well known to those skilled in the art. Alternatively, the DNA sample may be solubilized in solution with the oligonucleotide probe immobilized on a solid support, whereby the DNA sample may be contacted with the oligonucleotide probe by immersing the solid support having the oligonucleotide probe immobilized thereon in the solution containing the DNA sample.

The invention will now be illustrated by the following non-limiting Example.

EXAMPLE 1

Method of Detecting a DNA Mutation Associated with Canine Exercise-Induced Collapse The dynamin gene family encodes proteins that are essential for synaptic vesicle endocytosis. Exercise-induced collapse (EIC) in affected Labrador Retriever dogs is manifested by muscle weakness, incoordination, and life-threatening collapse after intense exercise. A whole genome scan of 143 affected dogs identified a locus on canine chromosome 9 with a LOD score of 12.2. SNP haplotype analysis confirmed the locus, and a strongly associated ($p<10^{-16}$) missense mutation in the dynamin 1 gene (DNM1) was identified. This Arg256Leu polymorphism is a compelling candidate causal mutation for EIC due to the critical function of dynamin 1 and its strong evolutionary conservation. This is the first naturally occurring mammalian DNM1 mutation to be identified and provides critical insight into synaptic vesicle biology across many species.

Materials and Methods:

Sample collection. This study was performed using protocols approved by the Institutional Animal Care and Use Committees (IACUC) of the University of Minnesota and the University of Saskatchewan. Written consent was obtained from all owners. Affected Labrador Retriever families were ascertained through affected offspring and we requested medical records, pedigrees, and DNA from all dog within 2 generations of affected dogs. The pedigrees for linkage analysis were assembled using CryillicSoftware. The Gentra Puregene™ DNA Isolation kit was used to extract genomic DNA from 3-6 mls of EDTA whole blood per manufacturer's instructions. The DNA was stored at −20° C.

Six different groups of dogs were identified based on available medical data and questionnaire information:
Group 1; Presumed affected; Dogs with a well-documented history of more than one collapse episode in which the pelvic limbs became ataxic and then flaccid.
Group 2; Recurrent collapse; Dogs with an incomplete description of the collapse episodes, but were, for the most part, consistent with the criteria for presumed affected.
Group 3; Single Collapse Episode; These dogs otherwise met the criteria for presumed affected.
Group 4; Atypical collapse; recurrent episodes of collapse, however the description did not entirely match with the criteria for classification of presumed affected.
Group 5; Alternative Collapse—other cause; Dogs for which another potential underlying cause of collapse was identified.
Group 6; No Collapse; Dogs never observed to collapse.

Microsatellite markers: Microsatellites were identified from published canine linkage and RH maps (R. Guyon et al., *Proc. Natl. Acad. Sci. U.S.A.* 100, 5296-5301 (2003); M. Breen et al., *BMC Genomics,* 13, 65 (2004)), and the UC-Davis canine linkage map (found on the world-wide-web at vgl.ucdavis.edu/research/canine/projects/linkage_map/data/) and in several cases from the CFA9 genome sequence (markers denoted KM/JM in Table 1). The reaction conditions contained 12.5 ng DNA, PCR Buffer with 1.5 mM $MgCl_2$ (QIAGEN®), 5 pmol forward primer, 1.5 pmol reverse primer containing a 20-mer tail sequence, 2 pmol fluorescently labeled primer which contained that 20-mer tail, 100 µM each of the dNTPs, 0.5 units HotStarTaq® DNA polymerase (QIAGEN®) in a final volume of 15 µL. PCR reactions were performed in 96 well plates with initial denaturation at 94° C. for 20 min; 35-40 cycles of 94° C. for 30 s, 56° C. for 30 s, and 72° C. for 30 s; and a final extension at 72° C. for 15 min. The products were size separated using the Beckman CEQ 8000 automated DNA analyzer.

Linkage analysis: 96 dogs (71 of them affected), from the pedigrees that contributed most of the statistical power in a simulated linkage analysis, were selected for the initial genotyping, and 252 dogs were ultimately included in finer mapping. 444 microsatellite markers spread across all 38 dog autosomes were chosen. The genotype data for all markers were checked for Mendelian inheritance through visual pedigree inspection. Genotypes were then entered into genetic analysis software and Mendelian inheritance was again confirmed through the linkage analysis programs. Two-point parametric linkage analysis was performed with FASTLINK software assuming an autosomal recessive mode of inheritance with 80% penetrance. The frequency of the normal allele was assumed to be 0.80 and the frequency of the affected allele was 0.20. The actual allele frequency and penetrance of the disease are not known for EIC, however we assume that the disease is not 100% penetrant because dogs only collapse after exposure to known triggering events. Allele frequencies and marker heterozygosity were calculated using 20 unrelated parents in the pedigrees. Significance levels for linkage were based on the thresholds proposed by Lander and Kruglyak (*Nature Genet.* 11, 241-247 (1995)). Significant evidence for linkage was a LOD score of 3.3 and suggestive evidence for linkage was a LOD score of 1.9. LOD scores of less than −2.0 excluded linkage to the locus.

SNP marker association and haplotype analysis: SNP markers within the 56-61 Mb region of CFA9 known to be informative in Labrador Retrievers were kindly provided by Dr Claire Wade of the Broad Institute of Harvard and MIT. A subset of these SNPs was genotyped on 303 Labrador Retrievers using the University of Minnesota Biomedical Genomics Center Sequenom platform. Primers were designed using SpectroDESIGNER software (M. Stephens et al., *Am. J. Hum. Genet,* 68, 978-989 (2001)). The SNP loci were amplified in four multiplex PCR reactions. PCR reactions contain 10 ng DNA, 0.5 µM each primer, 0.2 mM each dNTP, 1.5 mM $MgCl_2$, 3 units HotStarTaq® DNA polymerase (QIAGEN®). SNP genotype calls were filtered and aggressive calls omitted from the data set. SNPs with poor cluster analysis, minor allele frequency less than 0.001, and genotype calls in less than 75% of DNA samples were omitted, as were individual DNA samples with less than 75% genotype calls. A SNP within intron 3 of the PTGES2 gene was amplified with 5'-AGCCTGTGCGAAGTCTGG (SEQ ID NO:120) and 5'-CAGATCACCCAGTGAAGGAG (SEQ ID NO:121) primers to give a 392 by product, which was digested with restriction enzyme Ava 1. Missing genotypes and haplotype phase were inferred with PHASE version 2.1.1 software using the default parameters (M. Stephens et al., *Am. J. Hum. Genet.,* 68, 978-989 (2001)). A chi-square test was performed with the maximum unrelated subset of dogs within Haploview 4.0 CR2 to determine if significantly different allele frequency distributions existed for each SNP between affected/cases and control populations. Minimally conserved haplotype was also determined using Haploview 4.0 CR2. Data from individuals were imported as family linkage files. Haplotype blocks were manually extended across SNPs on either side of the DNM1 exon 6 non-synonymous SNP to determine the conserved haplotype around the DNM1 T767 and G767 alleles.

Genomic DNA sequencing: PCR primers were designed to amplify containing the positional candidate genes based on the known intron/exon boundaries of the human and/or canine gene. In several cases canine exons were not well annotated in comparison to other species, and the inventors used their best judgment as to their correct positioning for PCR primer design and sequencing. Initially two affected dogs and one unaffected dog were sequenced. PCR primer sequences for DNM1 analysis are provided in FIGS. 7A-7J. The reaction consisted of 25 ng genomic DNA, 40 µM dNTPs, 1.5 µL PCR buffer with 1.5 mM $MgCl_2$ (QIAGEN®), 0.2 units HotStarTaq® DNA polymerase (QIAGEN®), and 0.67 µM of each primer in a volume of 15 µL. The cycling conditions were an initial denaturation at 94° C. for 20 min; 30 cycles of 94° C. for 30 s, 56° C. for 30 s, 72° C. for 30 s; and a final extension at 72° C. for 15 min. PCR products were purified and sequenced in the forward and reverse directions at the Advanced Genetic Analysis Center of the University of Minnesota. Sequences were aligned with Sequencher™ software on a backbone of the assembled canine genome sequence (CanFam2.0), and the human RefSeq coding DNA sequences.

Genotyping the DNM1 G767T mutation: Intron based PCR primers Exon 6 F (GTAGGCTCTCCGACCCACTC (SEQ ID NO:122)) and Exon 6 R (TGAGGACACTAAC-CCCTGTTG (SEQ ID NO:123)) were used to generate a 337 by fragment that contained all of exon 6. Restriction enzyme Sml I (9.0 U with a 3 hour incubation at 55° C. cut the T767 allele to generate fragments of 165 and 172 bp, which were resolved by electrophoresis on a 2% agarose gel.

Results

Identification of the chromosomal locus: The inventors performed a whole genome scan with 444 microsatellite markers using families of 71 affected dogs. In this initial genome scan involving 96 dogs, the inventors identified one significantly linked marker—FH2885, 60.4 Mb position on canine chromosome 9 (CFA09)—with a log of odds (LOD) score of 3.67 at a theta of 0.10. Then they genotyped 15 additional CFA9 microsatellites between 55.5 and 63.4 Mb, which included 143 affected dogs and 109 unaffected relatives. Multiple markers in the region corresponding to the segment from approximately 57-60.5 Mb demonstrated significant linkage to EIC, while markers outside this region excluded linkage (Table 1). The LOD score for FH2885 increased to 8.31 at theta of 0.05 with the analysis of all 252 dogs. LOD scores in several instances were >12.0 at theta<0.05, with the maximum LOD score of 12.24 for the KM/JM3 marker at 58.5 Mb.

TABLE 1

Linkage of EIC to microsatellite markers on CFA09.

| Marker | Mb | LOD score and theta | Marker Heterozygosity |
|---|---|---|---|
| GALK1 | 7.849 | 0.22; 0.05 | 0.34 |
| FH2263 | 16.424 | −3.39; 0.10 | 0.88 |
| REN198P23 | 18.089 | −2.1; 0.05 | 0.50 |
| REN54L20 | 23.478 | −4.8; 0.10 | 0.64 |
| G06401 | 28.720 | −2.4; 0.10 | 0.46 |
| FH2186 | 34.797 | −2.0; 0.20 | 0.62 |
| FH3835 | 45.156 | −2.7; 0.10 | 0.55 |
| REN278L10 | 48.141 | −2.4; 0.05 | 0.65 |
| REN73K24 | 54.592 | −3.0; 0.05 | 0.47 |
| Davis0941 | 55.557 | 1.59; 0.10 | 0.38 |
| E04008 | 57.055 | −1.02; 0.05 | 0.39 |
| KM/JM1 | 57.243 | 9.98; 0.06 | 0.73 |
| Davis0943 | 57.470 | 1.70; 0.07 | 0.33 |
| KM/JM2 | 58.087 | 1.93; 0.10 | 0.37 |
| Davis0944 | 58.441 | 3.00; 0.05 | 0.26 |
| KM/JM3 | 58.548 | 12.24; 0.04 | 0.76 |
| KM/JM4 | 59.125 | 9.49; 0.05 | 0.65 |
| Davis0945 | 59.307 | 6.49; 0.07 | 0.57 |
| KM/JM5 | 59.523 | 10.46; 0.04 | 0.68 |
| KM/JM6 | 59.676 | 9.79; 0.06 | 0.67 |
| Davis0946 | 60.008 | 12.13; 0.03 | 0.73 |
| KM/JM9 | 60.287 | 9.15; 0.03 | 0.73 |
| FH2885 | 60.428 | 8.31; 0.5 | 0.73 |
| Davis0947 | 60.899 | 1.26; 0.10 | 0.47 |
| Davis0950 | 63.400 | 3.01; 0.09 | 0.78 |
| CAP09E | 64.200 | 0.49; 0.20 | 0.49 |

Genotypes were collected and analyzed for linkage to EIC as described in Materials and Methods. Markers up to the 54.59 position were run only on a group of 96 dogs; no markers gave positive LOD scores and the minimum LOD score and theta are reported. Markers from the 55.55-64.2 position were run on a group of 234 dogs and the maximum positive LOD score for each of these markers is reported. (Significant LOD scores >3.3 and positions are in bold).

Next the inventors analyzed 57 single nucleotide polymorphism (SNP) markers within the 56-61 Mb region of CFA9 on the inventors' entire collection of 303 related and unrelated Labrador retrievers. A chi-square test of independence was performed for the maximum unrelated subset of dogs to determine whether significantly different allele frequency distributions existed for each SNP between affected and control populations. Eighteen SNPs from the 57.25 to 60.0 Mb region had p-values<0.001, with the lowest p-value of $1.17 \times 10^{-11}$ (FIG. 4). The 58.4-60.0 Mb region became the focus of the inventors' attention due to the clustering of SNPs with low p values, a high frequency of homozygous genotypes in the EIC affected population, and unaffected dogs being heterozygous or homozygous for the alternate allele. This data was consistent with the hypothesis that EIC is a highly penetrant autosomal recessive trait, and the fact that our control population had many parents and sibs of affected dogs and would be expected to result in a high rate of heterozygosity.

The inventors sequenced four positional candidate genes out of 48 known or predicted genes in this region of CFA9 based on their biological function (FIG. 4). These were DNM1 (dynamin 1 at 58.62 Mb), PTGES2 (prostaglandin E2 synthase at 58.69 Mb), AK1 (adenylate kinase at 58.88 Mb), and SLC2A8 (neuronal glucose transporter at 59.28 Mb). Exonic SNPs were identified only in DNM1 and PTGES2 (FIGS. 7A-7J). All exonic SNPs in PTGES2 were synonymous and not associated with the EIC phenotype, while an intronic SNP gave a p value for association with EIC of only p=0.0099. However, several SNPs within the DNM1 gene were homozygous within the group of affected dogs.

DNM1 sequences and polymorphisms: The full length canine dynamin 1 protein predicted from the sequence data contains 864 amino acids while a short form predicted from possible alternative splicing contains 845 amino acids (FIGS. 1, 2 and 5A-5B). Five SNPs within the DNM1 amino acid coding DNA sequence were found, and four of these DNM1 SNPs were synonymous. An exon 6 G to T SNP at coding nucleotide position 767 resulted in the conversion of codon 256 from arginine to leucine (Arg256Leu). Twenty four additional dogs were examined for the G767T SNP: all twelve affected dogs were homozygous for the T767 allele, six unaffected dogs were homozygous for the G767 allele, and six unaffected dogs were heterozygous. This G767T DNM1 SNP produced a LOD score of 16.39 at a theta of 0.03, and a p-value for association of $1.07 \times 10^{-16}$.

Alignment of the wild type canine dynamin 1 amino acid sequence with human reveals a remarkable cross-species conservation. 860 of the 864 amino acids were identical, and of the four differences, only two (Q to H at codon 128, and A to T at codon 511) were non-conservative substitutions. There was also a high level of conservation in the amino acid sequence alignment of the 241-270 residue segment of canine dynamin 1 across multiple species and dynamins 2 and 3 (FIG. 3).

DNM1 genotype frequency: Table 2 presents the frequency of the three DNM1 genotypes for Labrador Retrievers in the different classification criteria.

TABLE 2

DNM1 genotypes in phenotyped Labrador Retrievers.

| | TT | GT | GG | Total | % TT |
|---|---|---|---|---|---|
| 1. Presumed Affected | 101 | 0 | 3 | 104 | 97% |
| 2. Collapse but with Incomplete data | 60 | 3 | 5 | 68 | 88% |
| 3. Single Collapse | 5 | 3 | 0 | 8 | 62% |
| 4. Atypical Collapse | 11 | 6 | 9 | 26 | 43% |
| 5. Collapse - Other Cause | 1 | 2 | 2 | 5 | 20% |
| 6. No Collapse | 12 | 65 | 55 | 132 | 9% |
| Parents of Presumed Affected | 5 | 15 | 0 | 20 | 25% |

Dogs were evaluated based on reported clinical signs and medical data questionnaires and placed into one of the collapse phenotype categories as described in Materials and Methods. Genotypes at coding nucleotide 767 of the canine DNM1 gene were determined as described in Materials and Methods.
In category 5 other potential causes of repeated collapse were cardiac arrhythmia for the TT genotype, laryngeal paralysis and lactic acidemia for the GT phenotypes, and metabolic myopathy and cardiac arrhythmia for the GG phenotypes.

Homozygous for the T767 allele were 97% of all dogs that fulfilled the study criteria for EIC and were presumed affected (group 1), and 88% of dogs with collapse consistent with EIC but with incomplete documentation (group 2). Dogs with a lower likelihood of having EIC, single reported collapse (group 3), atypical collapse (group 4), or another potential cause identified (group 5) had a decreasing likelihood of being homozygous for the T767 allele (62%, 43%, and 20% respectively). Twelve dogs that collapsed only once, or had collapse episodes that were less typical or incompletely described, were heterozygotes. Of 132 dogs for which the owners reported no episodes of collapse, 9% were homozygous for the T767 allele, 49% were heterozygous, and 42% were homozygous for the G767 allele. All 20 parents of affected dogs were heterozygous or homozygous for the T767 allele which is consistent with EIC being autosomal recessive. A significant false negative phenotyping rate, in which genetically susceptible dogs have not been exposed to conditions sufficient to initiate collapse, as well as the possibility of genetic and environmental modifying factors, may explain why 9% of dogs without a history of collapse are homozygous for the T767 allele.

Twelve heterozygotes were reported to have single collapse episodes or collapse episodes that did not fit the more stringent criteria for presumed affected (Table 2). This could be consistent with a less severe phenotype in carriers than for the homozygotes, and indicate the possibility of a partially penetrant dominant trait. There were, however, 65 heterozygotes with no known episodes of collapse, and the high frequency of heterozygotes in the population makes conclusions concerning genotype-phenotype relationships in heterozygotes ambiguous at present. In addition, since EIC is a diagnosis of exclusion, it is possible that the heterozygous collapsing dogs, as well as the homozygous G767 dogs that did collapse, could be phenocopies.

TABLE 3

DNM1 Genotypes in Retriever and Other Breeds

| | TT | GT | GG | Total | % TT |
|---|---|---|---|---|---|
| Labrador Retrievers (Field Trials) | 20 | 171 | 246 | 437 | 4.5% |
| Chesapeake Bay Retrievers | 1 | 4 | 20 | 25 | 4.0% |
| Curly-Coated Retrievers | 6 | 5 | 19 | 30 | 20% |
| Golden Retrievers | 0 | 0 | 7 | 7 | 0% |
| Border Collies | 0 | 1 | 45 | 46 | 0% |
| Leonbergers | 0 | 0 | 36 | 36 | 0% |
| Greyhounds | 0 | 0 | 4 | 4 | 0% |
| Cavalier King Charles Spaniels | 0 | 0 | 8 | 8 | 0% |

Retriever populations were solicited by attending field trial competition events in Minnesota, Wisconsin and North Dakota.
Samples from other breeds were sent by veterinarians and owners interested in EIC or had a dog exhibiting a form of collapse.
DNM1 genotypes were determined as described in Table 12

Minimally conserved SNP haplotype block: The inventors used SNP genotypes from 23 Labrador Retrievers with the strongest evidence of EIC to identify a minimally conserved haplotype block encompassing the T767 allele of the DNM1 gene (FIG. 6). The most common haplotype extended the entire 4.5 Mb segment of CFA9 for which SNPs were analyzed; however, an AAGTGGTG block that extended only 137 Kb in length was observed five times. The inventors then included all 413 chromosomes from all dogs with the DNM1 T767 allele and observed a large number of different shared haplotype lengths, but this same minimally conserved haplotype length of 137 Kb was observed over 99% of the time. There was no common haplotype observed at this locus for the 6% of affected dogs (categories 1 and 2) that were not T767 homozygotes. Similar analysis of 209 chromosomes containing the DNM1 G767 wild type allele found that the homologous unaffected AAGTGGGG haplotype was readily observed in a slightly larger block of 220-328 Kb. This was clearly the most commonly observed haplotype and was observed 33% of the time. Collectively, the minimally conserved SNP haplotype blocks suggest that the T767 allele arose from a common haplotype in Labrador Retrievers.

The likelihood that the DNM1 T767 allele has been present and identical by descent in canine populations for a large number of generations is also supported by its detection in several related breeds. The inventors have observed the identical 137 Kb haplotype in two related breeds, Chesapeake Bay Retrievers and Curly Coated Retrievers, both of which had DNM1 T767 allele homozygotes with reported collapse episodes. Lastly, the inventors have genotyped more than 400 Labradors from field trials conducted in the upper Midwest with dogs from 20 states and three Canadian provinces, and found a carrier frequency in this population of 30% and a homozygous affected frequency of 3%. A simple genotyping assay can now help Labrador breeders avoid producing affected puppies in future generations.

Dynamin structure, function and mutation: The DNM1 gene encodes a member of the dynamin subfamily of GTP-binding proteins that regulate clathrin-mediated endocytic vesicle formation. Dynamin 1 appears to be expressed exclusively in the brain and spinal cord, where it plays a key role in synaptic vesicle fission by assembling into collar-like structures around coated pits on the pre-synaptic terminal. These structures are severed to release coated vesicles, thereby re-forming synaptic vesicles to contain neurotransmitter and enabling continuous synaptic communication. Five major structural homology domains exist within the dynamin 1 protein. Amino acid residues from approximately 1-300 contain a GTPase domain, residues from approximately 205-505 contain the dynamin family central domain, residues 521-623 contain a Pleckstrin homology domain, and residues 624-750 contain a GTPase effector domain involved in self-assembly (20).

DNM1 knock-out mice are born alive, but postnatal viability is brief, due to inability to tolerate the neurological stimulation of everyday life. DNM2 and DNM3 may be constitutively expressed and can handle low frequency stimulation. DNM1 expression becomes essential when a heightened stimulus creates a heavy load on endocytosis and only as long as the stimulus persists. Dogs with EIC function normally at rest and with moderate exercise, but when exercised strenuously in a state of high excitement they become incoordinated and collapse. Rest results in complete recovery, presumably as dependence on DNM1 for neurotransmission is diminished. The Arg256Leu mutation in DNM1 associated with EIC is in the boundary region between the GTPase and central domains, for which the precise function is not yet clear. Induced mutations in the central domain or its boundary with the GTPase domain of orthologous DNM1 genes affect dynamin aggregation and assembly on membranes, and in some cases cause temperature-dependent loss of motor function at high ambient temperatures. To date, except for EIC in the Labrador Retriever, there are no other known naturally occurring DNM1 mutations in mammalian species. DNM2 mutations have already been associated with centronuclear myopathy and Charcot-Marie-Tooth disease that do not resemble EIC.

In conclusion, the inventors identified a DNM1 gene mutation that is very highly associated with EIC in the Labrador Retriever dog. This finding comes in close succession to the discovery of a SINE insertion mutation in the PTPLA gene responsible for centronuclear myopathy in this breed, and further demonstrates the utility of gene mapping in canine models. The Arg256Leu DNM1 mutation is a very compelling candidate causative mutation for EIC due to the essential function of the dynamin 1 protein in synaptic vesicle recycling and the strong evolutionary conservation of this protein across diverse species.

All publications are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method for determining whether a dog has or is predisposed to develop Exercise Induced Collapse (EIC) comprising:
   a) detecting in a nucleic acid sample from the dog the allele in the dynamin 1 gene at position 767 of SEQ ID NO: 1, and
   b) identifying that the dog has or is predisposed to the development of EIC when the dog is homozygous for the T767 allele.

2. The method of claim 1, wherein prior to or in conjunction with detection, the nucleic acid sample is subject to an amplification step.

3. The method of claim 2, wherein dynamin 1 or a portion thereof is amplified.

4. The method of claim 1, wherein the detecting step is by a) allele specific hybridization; b) size analysis; c) sequencing; d) hybridization; e) 5' nuclease digestion; f) single-stranded conformation polymorphism; g) primer specific extension; and/or h) oligonucleotide ligation assay.

5. The method of claim 4, wherein the detecting step is by size analysis, and the size analysis is preceded by a restriction enzyme digestion.

6. The method of claim 1, wherein the detecting step is by hybridization of the nucleic acid sample from the dog to at least one oligonucleotide probe specific for the dynamin 1 (G767T) allele is immobilized on a solid surface.

7. The method of claim 1, wherein the dog is a Labrador Retriever, Chesapeake Bay Retriever, Curly-Coated Retriever, or Border Collie.

8. A method for determining whether a dog has or is predisposed to developing an Exercise Induced Collapse (EIC), comprising:
   (a) transporting a biological sample from a dog suspected of having or being predisposed to developing EIC to a diagnostic laboratory,
   (b) detecting in a nucleic acid sample from the dog the allele in the dynamin 1 gene at position 767 of SEQ ID NO: 1
   (c) identifying that the dog has or is predisposed to the development of EIC when the dog is homozygous for the T767 allele and
   (d) providing results regarding whether the dog has the EIC associated allele.

* * * * *